(12) United States Patent
Frasier et al.

(10) Patent No.: US 11,089,975 B2
(45) Date of Patent: Aug. 17, 2021

(54) SYSTEMS, DEVICES AND METHODS FOR ENHANCING OPERATIVE ACCURACY USING INERTIAL MEASUREMENT UNITS

(71) Applicant: DePuy Synthes Products, Inc., Raynham, MA (US)

(72) Inventors: William Frasier, New Bedford, MA (US); Dennis Chien, West Chester, PA (US); Marc Puls, Landschaft (CH); Mark Hall, Bridgewater, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1045 days.

(21) Appl. No.: 15/475,587

(22) Filed: Mar. 31, 2017

(65) Prior Publication Data

US 2018/0279913 A1 Oct. 4, 2018

(51) Int. Cl.
*A61B 5/11* (2006.01)
*A61B 5/107* (2006.01)
(Continued)

(52) U.S. Cl.
CPC .............. *A61B 5/11* (2013.01); *A61B 5/107* (2013.01); *A61B 5/7271* (2013.01); *A61B 5/742* (2013.01);
(Continued)

(58) Field of Classification Search
CPC ...... A61B 2034/105; A61B 2034/2048; A61B 2034/2055; A61B 2034/2065;
(Continued)

(56) References Cited

U.S. PATENT DOCUMENTS 5,156,162 A 10/1992 Gerhardt
5,251,127 A 10/1993 Raab
(Continued)

FOREIGN PATENT DOCUMENTS

CN 1849101 A 10/2006
CN 103748763 A 4/2014
(Continued)

OTHER PUBLICATIONS

U.S. Appl. No. 16/434,166, filed Jun. 6, 2019, Method and Apparatus for Intraoperative Measurements of Anatomical Orientation US Continuation Application.
(Continued)

*Primary Examiner* — Amelie R Davis
(74) *Attorney, Agent, or Firm* — Barnes & Thornburg LLP

(57) ABSTRACT

Accuracy enhancing systems, devices and methods are provided using data obtained from inertial measurement units (IMUs). IMUs are provided on one or more of a patient, surgical table, surgical instruments, imaging devices, navigation systems, and the like. Data from sensors in each IMU is collected and used to calculate absolute and relative positions of the patient, surgical table, surgical instruments, imaging devices, and navigation systems on which the IMUs are provided. The data generated by the IMUs can be coupled with medical images and camera vision, among other information, to generate and/or provide surgical navigation, alignment of imaging systems, pre-operative diagnoses and plans, intra-operative tool guidance and error correction, and post-operative assessments.

25 Claims, 9 Drawing Sheets

(51) Int. Cl.
  *A61B 5/00*   (2006.01)
  *A61B 6/12*   (2006.01)
  *A61B 6/00*   (2006.01)
  *A61B 6/04*   (2006.01)
  *A61B 34/20*  (2016.01)
  *A61B 90/00*  (2016.01)
  *A61B 34/10*  (2016.01)

(52) U.S. Cl.
  CPC .............. *A61B 6/0492* (2013.01); *A61B 6/12* (2013.01); *A61B 6/4441* (2013.01); *A61B 6/4482* (2013.01); *A61B 6/461* (2013.01); *A61B 6/466* (2013.01); *A61B 6/505* (2013.01); *A61B 6/5294* (2013.01); *A61B 6/545* (2013.01); *A61B 6/547* (2013.01); *A61B 6/56* (2013.01); *A61B 6/589* (2013.01); *A61B 34/20* (2016.02); *A61B 6/0407* (2013.01); *A61B 6/0487* (2020.08); *A61B 6/5217* (2013.01); *A61B 2034/105* (2016.02); *A61B 2034/2048* (2016.02); *A61B 2034/2055* (2016.02); *A61B 2034/2065* (2016.02); *A61B 2090/363* (2016.02); *A61B 2090/372* (2016.02); *A61B 2090/376* (2016.02); *A61B 2090/3966* (2016.02); *A61B 2090/3983* (2016.02)

(58) Field of Classification Search
  CPC ........ A61B 2090/363; A61B 2090/372; A61B 2090/376; A61B 2090/3966; A61B 2090/3983; A61B 34/20; A61B 5/107; A61B 5/11; A61B 5/7271; A61B 5/742; A61B 6/0407; A61B 6/0457; A61B 6/0492; A61B 6/12; A61B 6/4441; A61B 6/4482; A61B 6/461; A61B 6/466; A61B 6/505; A61B 6/5217; A61B 6/5294; A61B 6/545; A61B 6/547; A61B 6/56; A61B 6/589
  See application file for complete search history.

(56) References Cited

U.S. PATENT DOCUMENTS

| | | | |
|---|---|---|---|
| 5,291,901 A | 3/1994 | Graf | |
| 5,305,203 A | 4/1994 | Raab | |
| 5,329,933 A | 7/1994 | Graf | |
| 5,748,767 A | 5/1998 | Raab | |
| 5,772,610 A | 6/1998 | McGorry et al. | |
| 6,015,409 A | 1/2000 | Jackson | |
| 6,514,219 B1 | 2/2003 | Guimond et al. | |
| 6,565,519 B2 | 5/2003 | Benesh | |
| 6,711,432 B1 | 3/2004 | Krause et al. | |
| 6,715,213 B2 | 4/2004 | Richter | |
| 7,001,346 B2 | 2/2006 | White | |
| 7,131,952 B1 | 11/2006 | Dickholtz, Sr. et al. | |
| 7,139,601 B2 | 11/2006 | Bucholz et al. | |
| 7,335,167 B1 | 2/2008 | Mummy | |
| 7,559,931 B2 | 7/2009 | Stone | |
| 7,611,522 B2 | 11/2009 | Gorek | |
| 7,634,119 B2 | 12/2009 | Tsougarakis et al. | |
| 7,634,306 B2 | 12/2009 | Sarin et al. | |
| 7,706,000 B2 | 4/2010 | Cohen et al. | |
| 7,918,887 B2 | 4/2011 | Roche | |
| 7,956,887 B2 | 6/2011 | Hoeg et al. | |
| 7,957,809 B2 | 6/2011 | Bourget et al. | |
| 7,974,677 B2 | 7/2011 | Mire et al. | |
| 7,981,115 B2 | 7/2011 | Justis et al. | |
| 8,057,479 B2 | 11/2011 | Stone | |
| 8,057,482 B2 | 11/2011 | Stone et al. | |
| 8,128,662 B2 | 3/2012 | Altarac et al. | |
| 8,167,823 B2 | 5/2012 | Nycz et al. | |
| 8,348,954 B2 | 1/2013 | Carls et al. | |
| 8,442,621 B2 | 5/2013 | Gorek et al. | |
| 8,535,337 B2 | 9/2013 | Chang et al. | |
| 8,549,888 B2 | 10/2013 | Isaacs | |
| 8,565,853 B2 | 10/2013 | Frigg et al. | |
| 8,690,888 B2 | 4/2014 | Stein et al. | |
| 8,888,821 B2 | 11/2014 | Rezach et al. | |
| 9,198,698 B1 | 12/2015 | Doose et al. | |
| 9,554,411 B1 | 1/2017 | Hall et al. | |
| 9,579,043 B2 | 2/2017 | Chien et al. | |
| 9,993,177 B2 | 6/2018 | Chien et al. | |
| 10,335,241 B2 | 7/2019 | Frasier et al. | |
| 10,396,606 B2 | 8/2019 | Hall et al. | |
| 10,499,996 B2 | 12/2019 | de Almeida Barreto | |
| 10,714,987 B2 | 7/2020 | Hall et al. | |
| 10,743,944 B2 | 8/2020 | Frasier et al. | |
| 10,820,835 B2 | 11/2020 | Gupta et al. | |
| 2002/0035321 A1 | 3/2002 | Bucholz et al. | |
| 2004/0152970 A1 | 8/2004 | Hunter et al. | |
| 2005/0033430 A1 | 2/2005 | Powers et al. | |
| 2005/0166410 A1 | 8/2005 | Richter et al. | |
| 2005/0222793 A1 | 10/2005 | Lloyd et al. | |
| 2005/0251026 A1 | 11/2005 | Stone | |
| 2005/0262911 A1 | 12/2005 | Dankowicz et al. | |
| 2006/0030771 A1 | 2/2006 | Levine et al. | |
| 2006/0100508 A1 | 5/2006 | Morrison | |
| 2006/0247773 A1 | 11/2006 | Stamp | |
| 2007/0060799 A1 | 3/2007 | Lyon et al. | |
| 2007/0106146 A1 | 5/2007 | Altmann et al. | |
| 2008/0103557 A1 | 5/2008 | Davis et al. | |
| 2008/0177203 A1 | 7/2008 | von Jako | |
| 2008/0228195 A1 | 9/2008 | von Jako et al. | |
| 2008/0269767 A1 | 10/2008 | O'Brien | |
| 2008/0292161 A1 | 11/2008 | Funk et al. | |
| 2009/0171328 A1 | 7/2009 | Horvath | |
| 2009/0249851 A1 | 10/2009 | Isaacs | |
| 2010/0010494 A1 | 1/2010 | Quimo | |
| 2010/0036384 A1 | 2/2010 | Gorek et al. | |
| 2010/0063508 A1 | 3/2010 | Borja et al. | |
| 2010/0069919 A1 | 3/2010 | Carls et al. | |
| 2010/0087823 A1 | 4/2010 | Kondrashov | |
| 2010/0100011 A1 | 4/2010 | Roche | |
| 2010/0191071 A1 | 7/2010 | Anderson et al. | |
| 2010/0191088 A1 | 7/2010 | Anderson et al. | |
| 2010/0204575 A1 | 8/2010 | Roche et al. | |
| 2010/0204955 A1 | 8/2010 | Roche et al. | |
| 2010/0312103 A1 | 12/2010 | Gorek et al. | |
| 2011/0040340 A1 | 2/2011 | Miller et al. | |
| 2011/0125196 A1 | 5/2011 | Quevedo et al. | |
| 2011/0196455 A1 | 8/2011 | Sieracki et al. | |
| 2011/0270262 A1 | 11/2011 | Justis et al. | |
| 2011/0275957 A1 | 11/2011 | Bhandari | |
| 2011/0295159 A1 | 12/2011 | Shachar et al. | |
| 2012/0035868 A1 | 2/2012 | Roche et al. | |
| 2012/0065497 A1 | 3/2012 | Brown et al. | |
| 2012/0095330 A1 | 4/2012 | Shechter et al. | |
| 2012/0112690 A1 | 5/2012 | Stulen et al. | |
| 2012/0123252 A1 | 5/2012 | Brunner | |
| 2012/0157019 A1 | 6/2012 | Li | |
| 2012/0172653 A1 | 7/2012 | Chornenky et al. | |
| 2012/0203140 A1 | 8/2012 | Malchau et al. | |
| 2012/0209117 A1 | 8/2012 | Mozes et al. | |
| 2012/0232834 A1 | 9/2012 | Roche et al. | |
| 2013/0079678 A1 | 3/2013 | Stein et al. | |
| 2013/0079679 A1 | 3/2013 | Roche et al. | |
| 2013/0079680 A1 | 3/2013 | Stein et al. | |
| 2013/0079793 A1 | 3/2013 | Stein et al. | |
| 2013/0131556 A1 | 5/2013 | Chantz | |
| 2013/0135312 A1 | 5/2013 | Yang et al. | |
| 2013/0165940 A1 | 6/2013 | DiSilvestro | |
| 2013/0241468 A1 | 9/2013 | Moshfeghi | |
| 2013/0268007 A1 | 10/2013 | Rezach et al. | |
| 2013/0303225 A1 | 11/2013 | Maguire | |
| 2014/0031829 A1 | 1/2014 | Paradis et al. | |
| 2014/0052149 A1 | 2/2014 | van der Walt et al. | |
| 2014/0057572 A1 | 2/2014 | Klinghult et al. | |
| 2014/0088607 A1 | 3/2014 | Recknor | |
| 2014/0148808 A1 | 5/2014 | Inkpen et al. | |
| 2014/0171965 A1 | 6/2014 | Loh et al. | |
| 2014/0232333 A1 | 8/2014 | Kim et al. | |
| 2014/0275981 A1 | 9/2014 | Selover et al. | |

(56) References Cited

U.S. PATENT DOCUMENTS

| | | |
|---|---|---|
| 2014/0276871 A1 | 9/2014 | Sherman et al. |
| 2014/0303522 A1 | 10/2014 | Akimoto et al. |
| 2014/0330112 A1 | 11/2014 | Wasielewski |
| 2015/0011874 A1 | 1/2015 | Amoako-Tuffour et al. |
| 2015/0057733 A1 | 2/2015 | Lotfi |
| 2015/0137746 A1 | 5/2015 | Lee et al. |
| 2015/0142372 A1 | 5/2015 | Singh |
| 2015/0150646 A1 | 6/2015 | Pryor et al. |
| 2015/0180263 A1 | 6/2015 | Sud et al. |
| 2015/0185846 A1 | 7/2015 | Otto et al. |
| 2015/0272694 A1 | 10/2015 | Charles |
| 2015/0305786 A1 | 10/2015 | Wehrle et al. |
| 2015/0313482 A1 | 11/2015 | Nabutovsky et al. |
| 2015/0313566 A1 | 11/2015 | Diers et al. |
| 2016/0007909 A1 | 1/2016 | Singh et al. |
| 2016/0058320 A1 | 3/2016 | Chien et al. |
| 2016/0058523 A1 | 3/2016 | Chien et al. |
| 2016/0191877 A1 | 6/2016 | Ono |
| 2016/0191887 A1* | 6/2016 | Casas ............ H04N 13/279 348/47 |
| 2016/0225192 A1 | 8/2016 | Jones et al. |
| 2016/0235480 A1 | 8/2016 | Scholl et al. |
| 2016/0262800 A1 | 9/2016 | Scholl et al. |
| 2016/0360997 A1 | 12/2016 | Yadav et al. |
| 2017/0143426 A1 | 5/2017 | Isaacs et al. |
| 2017/0189121 A1 | 7/2017 | Frasier et al. |
| 2017/0194820 A1 | 7/2017 | Hall et al. |
| 2017/0196507 A1 | 7/2017 | Singh et al. |
| 2017/0231709 A1 | 8/2017 | Gupta et al. |
| 2017/0348061 A1 | 12/2017 | Joshi et al. |
| 2018/0070860 A1 | 3/2018 | Gupta et al. |
| 2018/0256067 A1 | 9/2018 | Chien et al. |
| 2019/0090955 A1 | 3/2019 | Singh et al. |
| 2019/0321109 A1 | 10/2019 | Frasier et al. |
| 2019/0341818 A1 | 11/2019 | Hall et al. |
| 2020/0297432 A1 | 9/2020 | Frasier et al. |
| 2020/0303971 A1 | 9/2020 | Hall et al. |
| 2021/0059563 A1 | 3/2021 | Gupta et al. |

FOREIGN PATENT DOCUMENTS

| | | |
|---|---|---|
| CN | 104854533 A | 8/2015 |
| CN | 105011977 A | 11/2015 |
| EP | 1 943 954 A2 | 7/2008 |
| EP | 2 597 783 A2 | 5/2013 |
| EP | 2 901 957 A1 | 8/2015 |
| GB | 190927693 A | 9/1910 |
| JP | 2000-254141 A | 9/2000 |
| JP | 2003-523795 A | 8/2003 |
| JP | 2005-095433 A | 4/2005 |
| JP | 3746628 B2 | 2/2006 |
| JP | 4323276 B2 | 9/2009 |
| JP | 2010-233354 A | 10/2010 |
| JP | 2013-544144 A | 12/2013 |
| JP | 2015-109785 A | 6/2015 |
| WO | 99/15097 A2 | 4/1999 |
| WO | 2005/077000 A2 | 8/2005 |
| WO | 2013/053398 A1 | 4/2013 |
| WO | 2013/169674 A1 | 11/2013 |
| WO | 2014/025305 A1 | 2/2014 |
| WO | 2014/063181 A1 | 5/2014 |
| WO | 2015/003224 A1 | 1/2015 |
| WO | 2015/114119 A1 | 8/2015 |
| WO | 2015/162965 A1 | 10/2015 |
| WO | 2016/032875 A1 | 3/2016 |
| WO | 2019/055912 A1 | 3/2019 |

OTHER PUBLICATIONS

U.S. Appl. No. 16/515,005, filed Jul. 17, 2019, System and Methods for Wirelessly Powering or Communicating with Sterile-Packed Devices.

Baka, Nora, et al. "2D-3D shape reconstruction of the distal femur from stereo X-ray imaging using statistical shape models," Medical image analysis 15.6 (2011): 840-850.

Conn, K. S., M. T. Clarke, and J.P. Hallett, "A Simple Guide to Determine the Magnification of Radiographs and to Improve the Accuracy of Preoperative Templating," Bone & Joint Journal 84.2 (2002): 269-272.

Gorski, J.M., and Schwartz, L. "A Device to Measure X-ray Magnification in Preoperative Planning for Cementless Arthroplasty," Clinical Orthopaedics and Related Research 202 (1986): 302-306.

King, R. J., et al. "A Novel Method of Accurately Calculating the Radiological Magnification of the Hip," Bone & Joint Journal 91.9 (2009): 1217-1222.

Lamecker, Hans, Thomas H. Wenckebach, and H-C. Hege. ""Atlas-based 3D-shape reconstruction from X-ray images,"" Pattern Recognition, 2006. ICPR 2006. 18th International Conference on. vol. 1 IEEE, 2006; pp. 1-4.

Markelj, Primoz, et al. "A review of 3D/2D registration methods for image-guided interventions," Medical image analysis 16.3 (2012): 642-661.

Sarkalkan, Nazli, Harrie Weinans, and Amir A. Zadpoor, "Statistical shape and appearance models of bones," Bone 60 (2014): 129-140.

Schumann, S., Thelen, B., Ballestra, S., Nolte, L. P., Buchler, P., & Zheng, G., "X-ray Image Calibration and Its Application to Clinical Orthopedics," Medical Engineering & Physics (2014): 36(7), 968-974.

The, B., et al., "Digital Correction of Magnification in Pelvic X-rays for Preoperative Planning of Hip Joint Replacements: Theoretical Development and Clinical Results of a New Protocol," Medical Physics 32.8 (2005): 2580-2589.

Zheng, Guoyan, et al., "A 2D/3D correspondence building method for reconstruction of a patient-specific 3D bone surface model using point distribution models and calibrated X-ray images," Medical image analysis 13.6 (2009): 883-899.

Delorme, et al., Intraoperative comparison of two instrumentation techniques for the correction of adolescent idiopathic scoliosis. Rod rotation and translation. Spine (Phila Pa 1976). Oct. 1, 1999;24(19)2011-7.

Ghanem, et al., Intraoperative optoelectronic analysis of three-dimensional vertebral displacement after Cotrel-Dubousset rod rotation. A preliminary report. Spine (Phila Pa 1976). Aug. 15, 1997;22(16):1913-21.

International Search Report and Written Opinion for Application No. PCT/US2015/046217, dated Nov. 9, 2015 (11 pages).

International Search Report and Written Opinion for Application No. PCT/US2016/067134, dated Sep. 11, 2017 (20 pages).

International Search Report and Written Opinion for Application No. PCT/US2016/067140, dated Mar. 23, 2017 (13 pages).

International Search Report and Written Opinion for Application No. PCT/US2017/017344, dated Jul. 13, 2017 (22 pages).

Invitation to Pay Additional Fees for Application No. PCT/US2016/067134, dated Jun. 26, 2017 (14 pages).

Lafon, et al., Intraoperative three dimensional correction during in situ contouring surgery by using a numerical mode. Spine (Phila Pa 1976). Feb. 15, 2010;35(4):453-9. doi: 10.1097/BRS.0b013e3181b8eaca. Abstract.

Lafon, et al., Intraoperative three-dimensional correction during rod rotation technique. Spine (Phila Pa 1976). Mar. 1, 2009;34(5):512-9. doi: 10.1097/BRS.0b013e31819413ec.

Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.

Mac-Thiong, et al., A new technique for intraoperative analysis of trunk geometry in adolescent idiopathic scoliosis. Can J Surg. Jun. 2002;45(3):219-23.

Mac-Thiong, et al., The effect of intraoperative traction during posterior spinal instrumentation and fusion for adolescent idiopathic scoliosis. Spine (Phila Pa 1976). Jul. 15, 2004;29(14):1549-54.

Written Opinion for Application No. PCT/US2017/050023, dated Jan. 8, 2018 (4 Pages).

International Search Report and Written Opinion for Application No. PCT/US2018/024791, dated Aug. 6, 2018 (12 pages).

Extended European Search Report for Application No. 17849374.8, dated Mar. 31, 2020 (8 pages).

(56) References Cited

OTHER PUBLICATIONS

International Search Report for Application No. PCT/US2017/050023, dated Jan. 8, 2018 (6 Pages).
U.S. Appl. No. 16/892,955, filed Jun. 4, 2020, Method and Apparatus for Intraoperative Measurements of Anatomical Orientation.
U.S. Appl. No. 16/894,245, filed Jun. 5, 2020, Systems and Methods for Wirelessly Powering or Communicating With Sterile-Packed Devices.
Australian Office Action for Application No. 2016380934, dated Sep. 16, 2020 (6 pages).
Australian Office Action for Application No. 2016380934, dated Feb. 5, 2021, (5 pages).
Chinese Office Action for Application No. 201680077321.9, dated Jan. 6, 2021 (17 pages).
Japanese Office Action for Application No. 2018-534634, dated Nov. 10, 2020 (12 pages).
Mazzilli, F., et al. "Ultrasound Energy Harvesting System for Deep Implanted-Medical-Devices (IMDs)", 2012 IEEE International Symposium on Circuits and Systems (ISCAS),Seoul, 2012, pp. 2865-2868.

* cited by examiner

SYSTEMS, DEVICES AND METHODS FOR ENHANCING OPERATIVE ACCURACY USING INERTIAL MEASUREMENT UNITS

FIELD

The present application relates to inertial measurement units (IMUs), and more specifically, their use pre-, intra-, and post-operatively to achieve enhanced accuracy.

BACKGROUND

Traditionally, pre-, intra- and post-operative accuracy and success is determined using a combination of medical imaging and surgical navigation systems and devices. Medical imaging devices are systems or sets of systems that allow medical professionals to image anatomical areas of interest of a patient using imaging means such as computed tomography (CT), magnetic resonance (MR), angiography or fluoroscopy. Medical imaging devices include X-ray imaging systems and C-arm systems. Surgical navigation systems use a combination of medical imaging and cameras or other sensors to allow medical professionals to navigate the patient's anatomy during surgery.

To achieve optimal surgical results, the patient's anatomy is often medically imaged numerous times. For instance, if the patient is undergoing orthopedic surgery such as spine surgery, the patient can be exposed to (1) one or more X-ray images pre-operatively to ascertain the patient's condition and/or injury, identify the required type of surgery and operative parameters, and/or determine the exact state of the patient's spine near the date of surgery; (2) one or more X-ray images intra-operatively to assess the patient's spine at the time of surgery, provide navigation of surgical tools (e.g., guidewires, needles, drills, taps, drivers, etc.) as they are operated, and/or determine the accuracy of each surgical task as it is executed; and (3) one or more X-ray images post-operatively to assess the patient's spine after being operated on, determine the changes caused by the surgery, and/or ascertain the success of the surgery relative to a pre-operative plan. Such frequent medical imaging of the patient can expose the patient or medical staff to high doses of radiation, which can lead to serious medical risks such as cancer.

To minimize exposure to radiation, it is desirable to reduce to the number of medical images to which the patient is subjected. One way to reduce imaging of the patient is to avoid acquiring inaccurate or subpar images of the patient's target anatomy, which can be caused by misaligning the imaging system such that the target anatomy is not properly or optimally viewable by the imaging system. Traditional medical imaging systems such as C-arm systems are manually positioned to an optimal alignment, a task which is time consuming and subject to human error. Often, the medical imaging system must be aligned, removed to allow for the patient to be operated on, and returned to the same optimal position numerous times during surgery. And, at times, the medical imaging system must be aligned to multiple optimal positions during a single surgery, for instance, to align to different anatomical regions, such as different pedicles of the patient's spine during an orthopedic surgery. In an intra-operative environment where time and accuracy are even more critical, proper and precise alignment is of heightened importance. Moreover, these medical imaging and surgical navigation systems and devices are costly to purchase, maintain and operate.

Accordingly, there is a need for systems, methods and devices that provide medical imaging and/or surgical navigation while reducing exposure to radiation. There is also a need for such systems, methods and devices to be less expensive than traditional means, while providing enhanced operative accuracy.

SUMMARY

Systems and methods are provided for using inertial measurement units (IMUs) to enhance operative accuracy. In some example embodiments, enhanced operative accuracy includes providing operative assistance by outputting operational feedback. To generate the operational feedback, a three-dimensional (3D) representation of a patient's anatomy is generated from medical images of the patient. Operative parameters are calculated based on the generated 3D representation. IMUs are used to measure a relative location of the patient, and, in turn, other IMUs are used to measure the relative location of IMU-enabled tools. The output operational feedback is obtained based on the operative parameters and data obtained from the measurements of the IMUs.

In other example embodiments, enhanced operative accuracy includes providing pre-, intra- and post-operative assessments and/or feedback using IMUs positioned on or attached to a patient's anatomy, a surgical table, surgical instruments, or medical imaging and navigation systems and devices. IMU data obtained from sensors of the IMUs is used to calculate absolute and/or relative positions of the patient's anatomy, surgical table, surgical instruments, or medical imaging and navigation systems and devices. The IMU data can be combined with medical images, cameras and the like, for example, to provide surgical navigation, alignment and placement of instruments or devices, and to generate pre-operative plans, calculate operative parameters, determine intra-operative corrections, and assess post-operative changes.

In some embodiments, providing operative assistance includes receiving, from an imaging device, one or more medical images. The one or more medical images represent (1) one or more views of a patient anatomy, and (2) one or more markers of a known size. The size of the patient anatomy represented in the one or more medical images is calibrated based on the known size of each of the one or more markers. A three-dimensional (3D) representation of the patient anatomy is generated based on: (1) one or more anatomical images that match the patient anatomy represented in the one or more medical images, and (2) one or more anatomical landmarks identified on the one or more medical images and the 3D representation. Operative parameters are calculated based on the 3D representation of the patient anatomy, and first inertial measurement unit (IMU) data is received from a first set of IMUs. The real-world anatomy of the patient is matched to the 3D representation based on the first IMU data. Operational feedback is output based on one or more of (1) the operative parameters, and (2) second IMU data received from a second set of IMUs corresponding to one or more IMU-enabled tools.

In some embodiments, the one or more anatomical images that match the patient anatomy can be identified from among a set of existing anatomical images stored in a communicatively coupled database or atlas, and can be matched to the patient anatomy using a best fit method.

In some embodiments, the operative parameters can include one or more of (1) a bone anchor insertion location, (2) a bone anchor trajectory, and (3) a bone anchor depth.

The operative parameters can be measured relative to the 3D representation of the patient anatomy.

In some embodiments, the first set of IMUs can be positioned on the patient and/or a surgical table corresponding to the patient in a first orientation relative to the patient. The first IMU data can include the absolute location of each of the IMUs.

In some embodiments, calculating the relative location of each of the IMUs in the first set of IMUs is based on the first IMU data. The first IMU data can include the relative location of each of the IMUs.

In some embodiments, matching the real-world anatomy of the patient to the 3D representation comprises: providing prompts to contact points on the real-world anatomy of the patient using one of the IMU-enabled tools, and associating the contact points of the real-world anatomy to corresponding points on the 3D representation.

In some embodiments, the output of the operational feedback can cause the operational feedback to be rendered on a display device. The operational feedback can comprise a visual representation of the one or more IMU-enabled tools superimposed over the 3D representation, at their respective locations relative to the patient anatomy. The operational feedback can further comprise a visual representations of the operative parameters. In some embodiments, the database or atlas of existing anatomical images can be stored in at least one memory.

In some embodiments, a surgical navigation system includes one or more IMU-enabled instruments, a camera, an IMU-based assistance system. The IMU-enabled instruments intra-operatively collect IMU data from each IMU of the IMU-enabled instruments. The camera tracks the intra-operative movement and location of the one or more IMU-enabled instruments. The IMU-based assistance system provides operational feedback by: determining the existence of an error in the tracking of the movement and location of one of the one or more IMU-enabled instruments; collecting the IMU data from the at least the one of the one or more IMU-enabled instruments; and supplementing the tracking of the movement and location of the one of the one or more IMU-enabled instruments using the IMU data. The IMUs of each of the one or more IMU-enabled instruments can be embedded or removably attached thereto. The camera can include an IMU.

In some embodiments, the existence of an error can be triggered by one or more of (1) the angle of one or more of the IMU-enabled instruments relative to the line of sight of the camera exceeding a threshold, (2) one or more of the IMU-enabled instruments being outside of the line of sight of the camera, and (3) the camera malfunctioning.

In some embodiments, providing the operational feedback can include calculating a correction factor for the one of the one or more IMU-enabled instruments based on the IMU data. The supplementing of the tracking of the movement and location of the one of the one or more IMU-enabled instruments further uses the correction factor.

In some embodiments, the one or more IMU-enabled instruments can include colored markers, and the camera tracks the movement and location of the one or more IMU-enabled instruments by identifying the colored markers of each of the one or more IMU-enabled instruments.

In some embodiments, the IMU data can include the absolute location of each of the one or more IMU-enabled instruments and the relative location of each of the one or more IMU-enabled instruments. The relative location of each of the one or more IMU-enabled instruments can indicate their location relative to one or more of (1) the one or more IMU-enabled instruments, (2) the camera, and (3) a patient anatomy, as visualized by the camera.

In some embodiments, a surgical navigation method includes providing operational feedback by: determining the existence of an error in the tracking of the movement and location of an IMU-enabled instrument performed using a camera, the IMU-enabled instrument comprising an IMU and being operable to intra-operatively collect IMU data therefrom; collecting the IMU data from the IMU-enabled instrument; and supplementing the tracking of the movement and location of the one of the one or more IMU-enabled instruments using the IMU data. The IMU of the IMU-enabled instrument can be embedded or removably attached thereto. The IMU data can comprise the absolute location of the IMU-enabled instrument and the relative location of the IMU-enabled instrument. The camera can comprise an IMU.

In some embodiments, the existence of an error can be triggered by one or more of (1) the angle of the IMU-enabled instrument relative to the line of sight of the camera exceeding a threshold, (2) the IMU-enabled instrument being outside of the line of sight of the camera, and (3) the camera malfunctioning.

In some embodiments, providing of the operational feedback can further comprise calculating a correction factor for the IMU-enabled instrument based on the IMU data. The supplementing of the tracking of the movement and location of the IMU-enabled instrument can further use the correction factor.

In some embodiments, the IMU-enabled instrument can comprise colored markers, and the camera can track the movement and location of the IMU-enabled instrument by identifying the colored markers of the IMU-enabled instrument.

In some embodiments, the relative location of the IMU-enabled instrument indicates its location relative to one or more of (1) other IMU-enabled instruments, (2) the camera, and (3) a patient anatomy, as visualized by the camera.

In some embodiments, an IMU-based assistance system can include at least one memory and a processor coupled to the at least one memory. First IMU data is collected from a plurality of IMUs attached to a patient engaged in a first physical position at a first instance. The patient's first attributes are calculated based on the first IMU data. The first IMU data and the first attributes are stored in the at least one memory. Second IMU data is collected from the plurality of IMUs attached to the patient engaged in the first physical position at a second instance after the first instance. The patient's second attributes are calculated based on the second IMU data. And, changes to an anatomy of the patient are identified by comparing the first attributes to the second attributes. In some embodiments, the first instance can occur pre-operatively, and the second instance can occur intra-operatively or post-operatively.

In some embodiments, the plurality of IMUs are attached to the patient at skin level using one or more of straps, adhesives or clothing apparel.

In some embodiments, the first attributes and the second attributes of the patient each include the flexibility of the patient.

In some embodiments, standard measurements are received from the at least one memory or over a network. The first IMU data or first attributes are compared to the standard measurements. A condition of the patient is assessed based on the comparison of the first IMU data or first attributes to the standard measurements.

In some embodiments, An IMU-based assistance system includes at least one memory and a processor communicatively coupled to the at least one memory. First IMU data is collected from a plurality of IMUs attached to a patient engaged in a first physical position at a first instance. The patient's first attributes are calculated based on the first IMU data The first IMU data and the first attributes are stored in the at least one memory. Second IMU data is collected from the plurality of IMUs attached to the patient engaged in the first physical position at a second instance after the first instance. The patient's second attributes are calculated based on the second IMU data. Changes to an anatomy of the patient are identified by comparing the first attributes to the second attributes.

In some embodiments, the first instance can occur pre-operatively, and the second instance can occur intra-operatively or post-operatively.

In some embodiments, the plurality of IMUs can be attached to the patient at skin level using one or more of straps, adhesives or clothing apparel.

In some embodiments, the first attributes and the second attributes of the patient each can include the flexibility of the patient.

In some embodiments, the standard measurements are retrieved from the at least one memory or over a network. The first IMU data or first attributes are compared to the standard measurements. A condition of the patient is assessed based on the comparison of the first IMU data or first attributes to the standard measurements.

In some embodiments, a system for providing IMU-based alignment includes a medical imaging device for imaging a patient and an IMU-based assistance system. The medical imaging device is movable relative to the patient or a surgical table having a first set of IMUs attached thereto. The medical imaging device can include an imaging source and an imaging detector having a second set of IMUs attached thereto. The IMU-based assistance system is communicatively coupled to the medical imaging device, and provides alignment of the medical imaging device by: receiving first IMU data from the second set of IMUs, the first IMU data comprising information obtained when the medical imaging device is in a first position; receiving second IMU data from the second set of IMUs, the second IMU data comprising information obtained when the medical imaging device is in a second position; and calculating a relative position of the medical imaging device in the second position measured relative to (1) the medical imaging device in the first position, or (2) the patient or the surgical table.

In some embodiments, the medical imaging device is a C-arm comprising an emitter and a detector at each end of the C-arm.

In some embodiments, the first set of IMUs are attached to the emitter and the detector of the C-arm.

In some embodiments, the IMU-based assistance system can provide the alignment of the medical imaging device by (1) guiding the medical imaging device from the first position to the second position, after calculating the relative position of the medical imaging device in the second position; and/or (2) driving the C-arm from the first position to the second position, after calculating the relative position of the medical imaging device in the second position.

In some embodiments, in the first position, the medical imaging device is at a ground position away from the patient, and in the second position, the medical imaging device is aligned to image a first portion of the patient.

In some embodiments, the first IMU data and the second IMU data can include location information of the medical imaging device.

In some embodiments, the IMU-based assistance system can provide intra-operative feedback via a display device, the intra-operative feedback indicating the position of one or more IMU-enabled instruments relative to the patient. The intra-operative feedback can be generated based on third IMU data received from the one or more IMU-enabled instruments.

BRIEF DESCRIPTION OF DRAWINGS

This disclosure will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems, devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. Further, to the extent features or steps are described as being, for example, "first" or "second," such numerical ordering is generally arbitrary, and thus such numbering can be interchangeable.

The present disclosure includes some illustrations and descriptions that include prototypes or bench models. A person skilled in the art will recognize how to rely upon the present disclosure to integrate the techniques, systems, devices, and methods provided for into a product, such as a consumer ready, warehouse-ready, or operating room ready surgical system.

A person skilled in the art will appreciate that the present disclosure has application in conventional endoscopic, minimally-invasive, and open surgical procedures as well application in robotic-assisted surgery.

Exemplary embodiments of the present disclosure provide enhanced operative assistance. Measurement data from sensors in IMUs is collected pre-, intra- and/or post-operatively. The IMUs are attached or equipped on one or more of a patient's anatomy, a surgical table, surgical instruments, or medical imaging and navigation systems and devices. The data obtained from the IMUs can be used to calculate the absolute position of the IMUs and their corresponding objects, and/or relative locations therebetween. The data received from the IMUs, including the calculated absolute and relative locations, can be coupled with medical images, information obtained from cameras, and other data to provide, among other things, surgical navigation, alignment of imaging devices, pre-operative plans, intra-operative corrections and post-operative assessments.

System

Figure 1:
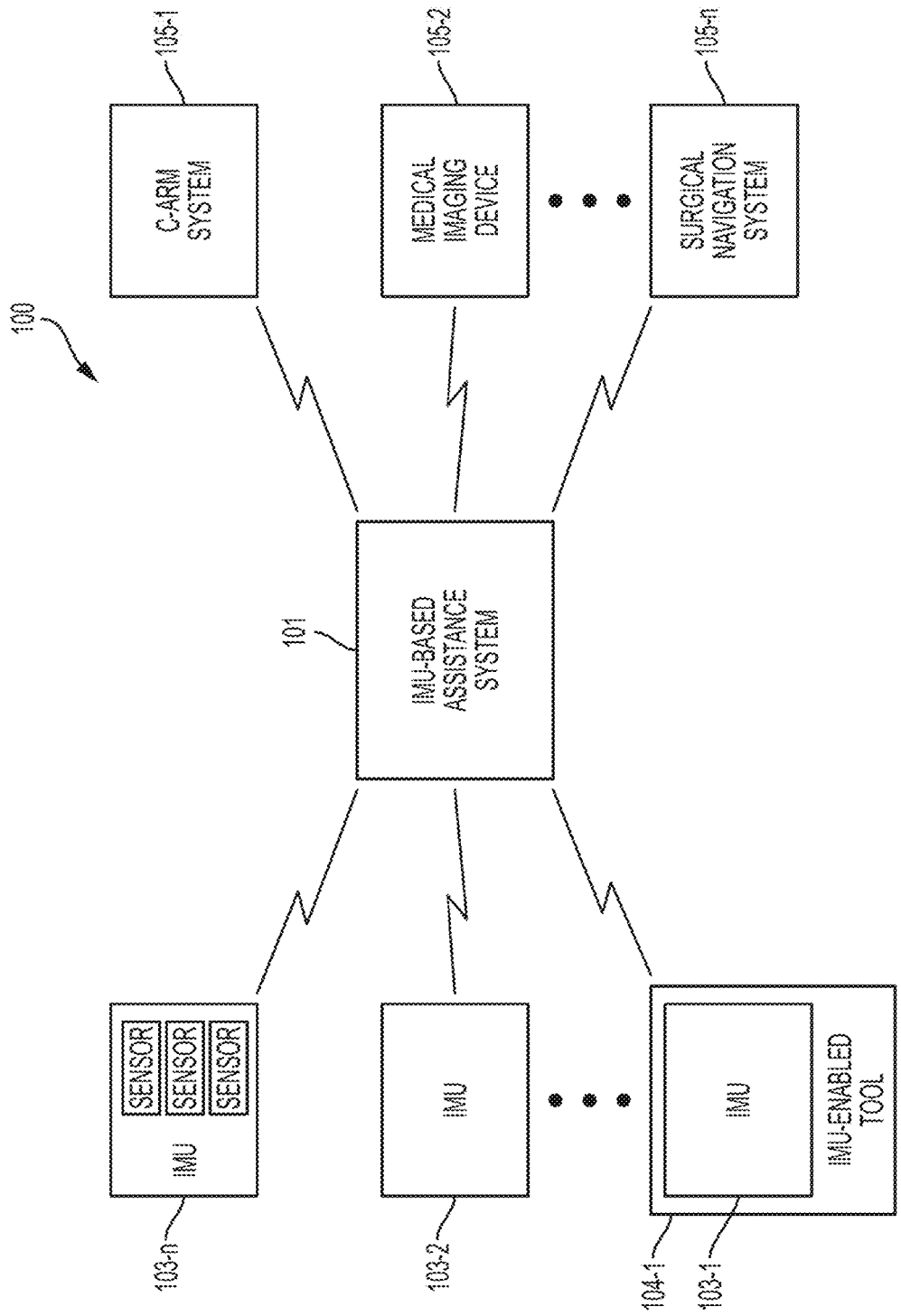
FIG. 1 is a diagram of an exemplary embodiment of a system architecture including an IMU-based assistance system.

FIG. 1 illustrates one exemplary embodiment of a system architecture 100 for providing IMU-based assistance in pre-, intra-, and post-operative environments. As shown, system architecture 100 includes an IMU-based assistance system 101 communicatively coupled to IMUs 103 and medical devices and systems 105.

An IMU is an electronic device equipped with sensors that can detect and report information about an object to which the IMU is attached. The sensors in an IMU can include one or more accelerometers, gyroscopes and magnetometers that can measure an object's attributes including, for example, its specific force, angular rate, magnetic field, rotation (e.g., pitch, yaw, roll), acceleration, position, location, and angular reference. The sensors can be 3-axis sensors.

The IMUs 103 include IMUs 103-1, 103-2, . . . , and 103-$n$ (collectively referred to as "IMUs" and/or "103"). Each of the IMUs 103 can be a stand-alone IMU such as IMUs 103-2 and 103-$n$, or can be equipped on medical or surgical tools or instruments (hereinafter referred to as "IMU-enabled tools" or "IMU-enabled instruments"), such as IMU 103-1. It should be understood that although three IMUs are illustrated in FIG. 1, any number of IMUs and IMU-enabled tools can exist and be communicatively coupled to the IMU-based assistance system 101.

As shown in FIG. 1, the IMU 103-1 is equipped on an IMU-enabled tool 104-1. IMU-enabled tools are instruments, devices or the like that can be used in surgical environments. Non-limiting examples of tools used in orthopedic surgical environments, which can be IMU-enabled, include guidewires, needles, taps, drivers, drills, cutters, blades, bone skids, retractors, access devices, and forceps, as well as implants such as bone anchors, spacers, cages, rods, plates, connectors, and the like. In some embodiments, an IMU-enabled tool can be an array that includes multiple surgical tools. Each of the tools can be manufactured with an IMU or can have an IMU added to it, permanently or removably, at a later time after being manufactured.

The IMUs 103 can transmit data collected by their respective sensors to other communicatively coupled systems and devices via wired or wireless means of communication known by those of skill in the art. For instance, the IMUs 103 can communicate with each other, with the IMU-based assistance system 101 or with medical devices and systems 105. In some embodiments, IMUs with wireless communication capabilities can communicate with each other and with other systems and devices using Wi-Fi, near field communication (NFC), Bluetooth and other short-range radio frequency means known by those of skill in the art.

The medical devices and systems 105 can include one or more of a C-arm system 105-1, a medical imaging device 105-2, and a surgical navigation system 105-$n$, although it should be understood that any number and types of devices and systems used in surgical environments can be included among the medical devices and systems 105. Each of the medical devices and systems 105 can include one or more of processors, memory, display devices, and wired and/or wireless communication means. The C-arm system 105-1 is a fluoroscopic X-ray system used for diagnostic and surgical procedures. The medical imaging device 105-2 can be an X-ray machine for generating medical images of a patient in a pre-operative environment. It should be understood that, in some embodiments, the C-arm system 105-1 and medical imaging device 105-2 can utilize other imaging means known in the art including computed tomography (CT), magnetic resonance (MR), angiography or fluoroscopy. The surgical navigation system 105-$n$ is a system made up of various instruments that can be tracked in relation to each other and the patient. The C-arm system 105-1, medical imaging device 105-2 and surgical navigation system 105-$n$ are described in further detail below with reference to FIGS. 2 to 9.

In some embodiments, the IMU-based assistance system 101 is a stand-alone system that includes one or more of a processor, memory, display device and communication means. For example, the IMU-based assistance system 101 can be integrated, embedded or implemented, partially or completely, in a personal computing device, mobile computing device, tablet, or the like. As described in further detail below with reference to FIGS. 2 to 9, the display device of the system 101 outputs, displays or renders information, including data obtained by the system 101 from the IMUs 103 and/or medical devices and system 105, or data calculated or generated by the system 101. In other embodiments, the IMU-based assistance system 101 is part of, housed together with, embedded or integrated in an IMU (e.g., IMU 103-2, 103-$n$), IMU-enabled tool (e.g., IMU 103-1) and/or one of the medical devices and systems 105. In such scenarios, the system 101 can use or share the memory, processor, display and/or communication means of the IMU, IMU-enabled tool or of the medical devices and systems.

It should be understood that one or more of the IMU-based assistance system 101, the IMUs 103 or IMU-enabled tools, and the medical devices and systems 105 can be operated or interacted with by a human or by robotic systems.

First Embodiment

Figure 2:
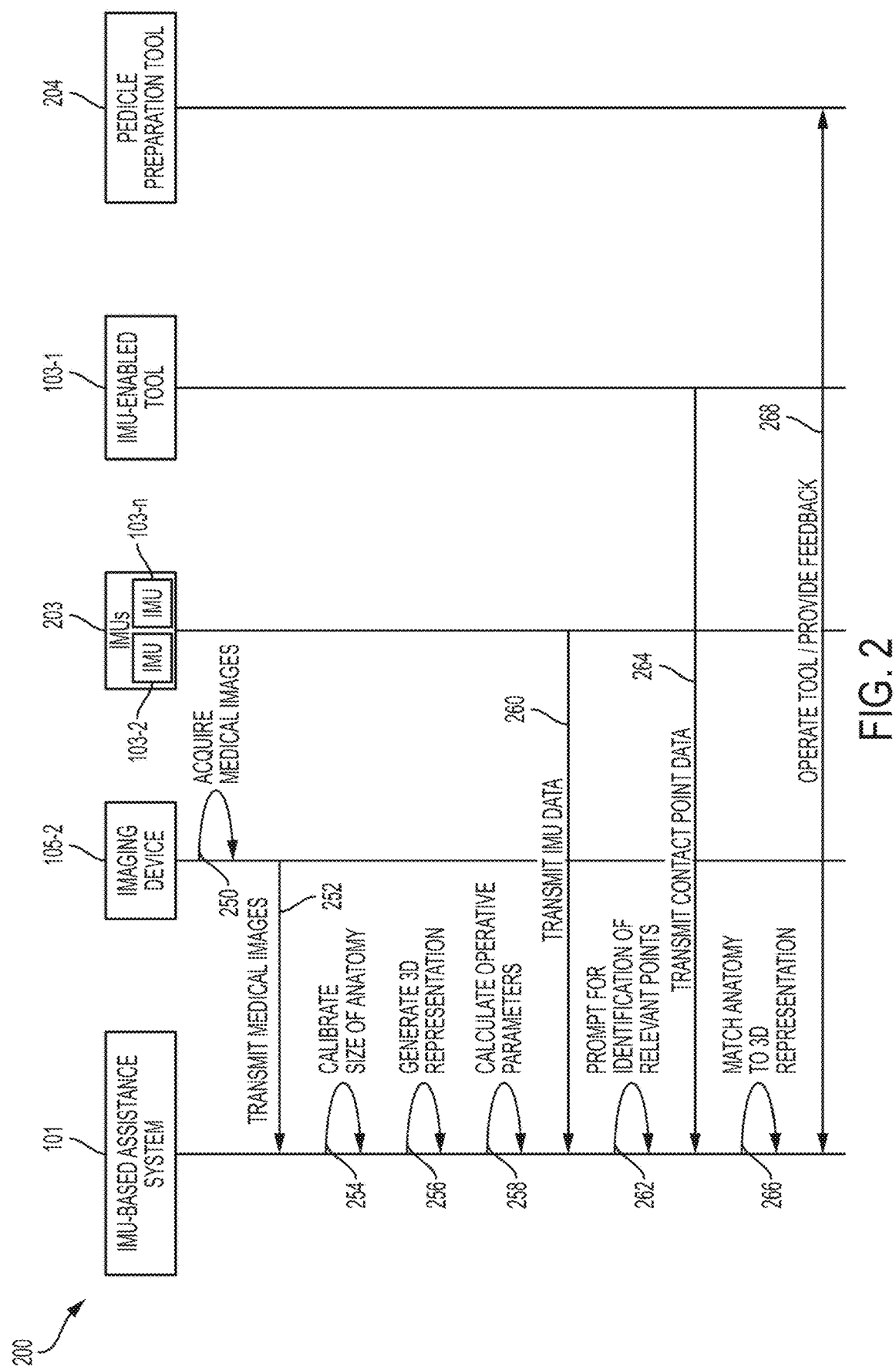
FIG. 2 is a sequence diagram of an exemplary embodiment of a process for using an exemplary configuration of the IMU-based assistance system.

FIG. 2 is a sequence diagram 200 illustrating one exemplary embodiment of a configuration of the IMU-based assistance system 101 for providing intra-operative feedback. More specifically, in the exemplary embodiment described in connection with FIG. 2, the intra-operative feedback provided by the IMU-based assistance system 101 includes guidance for inserting or implanting a bone anchor (e.g., a pedicle or lateral mass screw). As shown at step 250, the imaging device 105-2 acquires medical images of a patient in a pre-operative environment. The medical images obtained at step 250 are X-rays, although the medical images can be acquired using a variety of technologies and techniques known in the field, including magnetic resonance (MR), computed tomography (CT) and fluoroscopy.

In some embodiments, the medical images obtained at step 250 are acquired from the patient while the patient is in a standing position, though it should be understood that the patient can be imaged in any position. The medical images are a visual representation of views of the patient, such as an anterior to posterior view and a lateral view. The patient is imaged using one or more radiographic film identification markers, such as X-ray markers or the like commonly known in the field, that, along with the patient, are also visually represented on the medical images. Markers may also be established after an image is taken with manual or automated techniques based on identification of anatomical features, as is understood by those skilled in the art. Characteristics such as the size of the X-ray markers are either known or able to be calculated by the imaging device 105-2 and/or the IMU-based assistance system 101.

Figure 3:
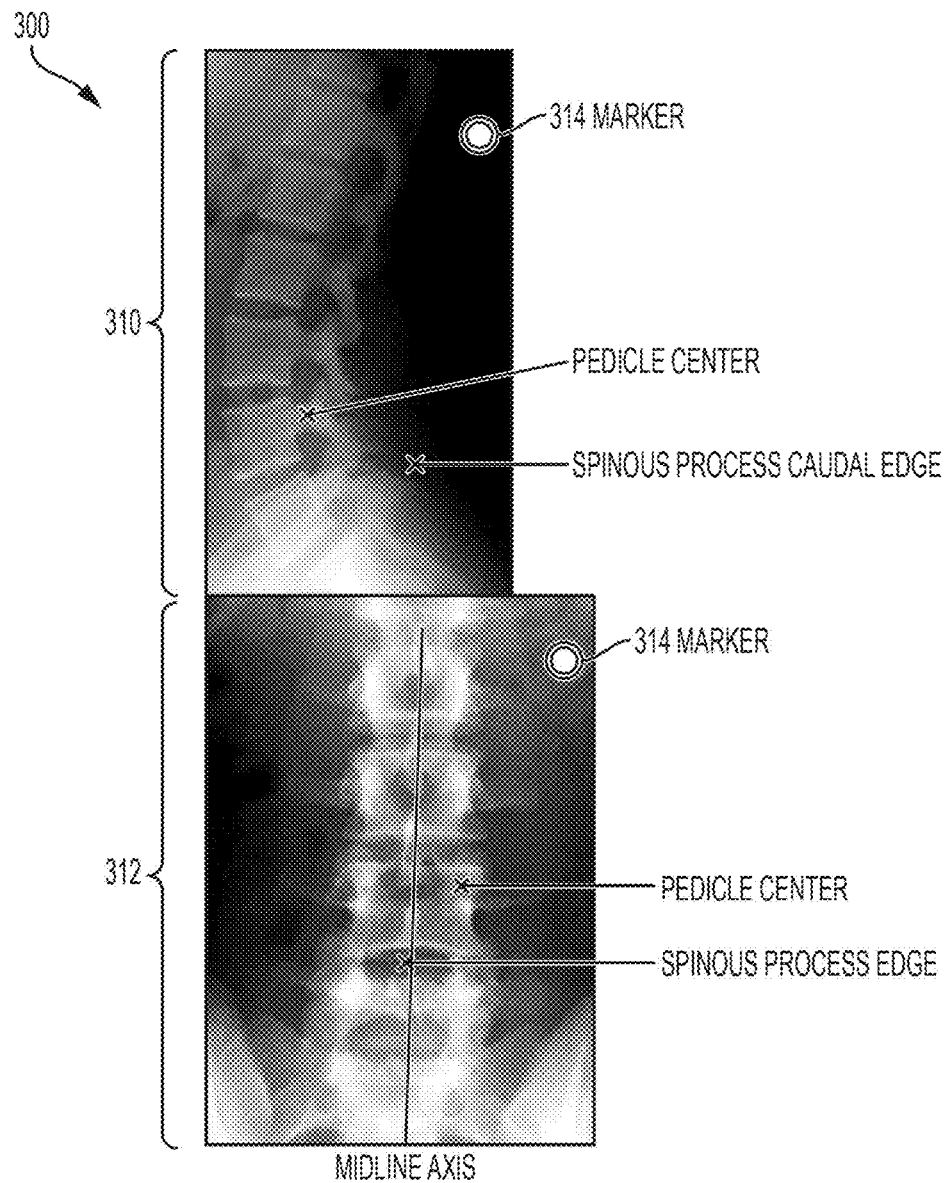
FIG. 3 is an exemplary embodiment of medical images representing a lateral and a posterior-to-anterior view of a patient.

FIG. 3 illustrates one exemplary embodiment of medical images 310 and 312, which are X-rays representing a lateral view and an anterior to posterior view, respectively, of a patient's spine. Identified in the medical images 310 and 312 are the patient's pedicle center and spinous process edge. Each of the medical images 310 and 312 also includes a visual representation of a marker 314 used during the generation of the X-rays or generated during X-ray review with a manual or automated method of anatomical feature identification. As is described in detail in connection with the flow chart 200, medical images such as the medical images 310 and 312 are used to provide intra-operative feedback of the patient.

The medical images 310 and 312 are transmitted from the imaging device 105-2 to the IMU-based assistance system 101, at step 252. The medical images can be transmitted by wired or wireless communication means. In some embodiments, the medical images are transmitted to the IMU-based assistance system 101 by photographing the medical images using a camera or other input or imaging device of the IMU-based assistance system 101. In some embodiments, the medical images are transmitted as or compiled into a single medical image. Hereinafter, a medical image can refer to a grouping of one or more medical images (or photographs of medical images) representing one or more views of the patient.

Using the medical image obtained at step 252, the IMU-based assistance system 101 calibrates, at step 254, the size of the anatomy (or part of the body of the patient) visually represented in the medical image. For example, to calibrate the size of the anatomy, the system 101 identifies the marker used during the imaging of the patient at step 250, and which is visually represented in the medical image, and retrieves or calculates its size. Having the size of the marker enables the system 101 to calculate attributes of the visually represented anatomy and the medical image, such as its magnification factor and the distance from the patient at which the medical image was acquired. It should be understood that various calibration algorithms known by those skilled in the art can be used at step 252. Examples of such algorithms for computing X-ray magnification and calibration are described, for instance, in Gorski, J. M., and Schwartz, L. "A Device to Measure X-ray Magnification in Preoperative Planning for Cementless Arthroplasty," Clinical Orthopaedics and Related Research 202 (1986): 302-306; Conn, K. S., M. T. Clarke, and J. P. Hallett, "A Simple Guide to Determine the Magnification of Radiographs and to Improve the Accuracy of Preoperative Templating," Bone & Joint Journal 84.2 (2002): 269-272; The, B., et al., "Digital Correction of Magnification in Pelvic X-rays for Preoperative Planning of Hip Joint Replacements: Theoretical Development and Clinical Results of a New Protocol," Medical Physics 32.8 (2005): 2580-2589; King, R. J., et al. "A Novel Method of Accurately Calculating the Radiological Magnification of the Hip," Bone & Joint Journal 91.9 (2009): 1217-1222; Schumann, S., Thelen, B., Ballestra, S., Nolte, L. P., Büchler, P., & Zheng, G., "X-ray Image Calibration and Its Application to Clinical Orthopedics," Medical Engineering & Physics (2014): 36(7), 968-974, the contents of which are incorporated by reference herein in their entireties.

In turn, at step 256, a three-dimensional (3D) representation of the anatomy calibrated at step 254 is generated. The 3D representation is created by matching the calibrated anatomy to existing two- and three-dimensional anatomical images corresponding to the type of the calibrated anatomy. The existing anatomical images used for generating the 3D representation are obtained from one or more databases, atlases, or repositories of images stored and managed by the system 101 or by a third-party provider system that is communicatively coupled to the IMU-based assistance system 101. In some embodiments, generating the 3D representation of the calibrated anatomy is performed using a best fit method that identifies one or more two- or three-dimensional anatomical images from the databases, atlases or repositories of images that most closely match or resemble the calibrated anatomy. The identified matching or resembling images may be used alone, or in combination with one another, to generate the 3-D representation of the calibrated anatomy. Examples of such algorithms for identifying anatomical images include bone morphing algorithms based on atlas geometries and/or statistical shape models, including those described, for instance, in Baka, Nora, et al. "2D-3D shape reconstruction of the distal femur from stereo X-ray imaging using statistical shape models," Medical image analysis 15.6 (2011): 840-850; Markelj, Primoz, et al. "A review of 3D/2D registration methods for image-guided interventions," Medical image analysis 16.3 (2012): 642-661; Lamecker, Hans, Thomas H. Wenckebach, and H-C. Hege. "Atlas-based 3D-shape reconstruction from X-ray images," Pattern Recognition, 2006. ICPR 2006. 18th International Conference on. Vol. 1. IEEE, 2006; Sarkalkan, Nazli, Harrie Weinans, and Amir A. Zadpoor, "Statistical shape and appearance models of bones," Bone 60 (2014): 129-140; and Zheng, Guoyan, et al., "A 2D/3D correspondence building method for reconstruction of a patient-specific 3D bone surface model using point distribution models and calibrated X-ray images," Medical image analysis 13.6 (2009): 883-899, the contents of which are incorporated by reference herein in their entireties.

In some embodiments, the process of generating the 3D representation described in connection with step 256 is aided by (1) the identification of specific anatomical landmarks on the patient's anatomy represented in the medical image, and (2) the matching of the identified anatomical landmarks to corresponding points on the generated 3D representation. Using this information, and information (e.g., size of anatomy) calculated using the marker in the medical image, the medical image of the patient's anatomy can be more accurately mapped to the 3D representation. This identification and matching can also allow the system 101 to corroborate the accuracy or errors in the 3D representation, and take remedial measures to ensure that the final, resulting 3D representation is as optimal and representative of the calibrated anatomy as possible.

Moreover, this identification and matching of anatomical landmarks may be performed using one or more of computing devices, robotic systems or humans. For instance, in some embodiments, the medical image and a 3D representation of the calibrated anatomy are graphically rendered by a display device of the IMU-based assistance system 101, either simultaneously or sequentially. The display device prompts a user to identify specified anatomical landmarks in the graphically rendered medical image. The user can be any of a variety of medical professionals capable of accurately identifying the required landmarks. For example, when the anatomy represented in the medical image is a spine or a portion thereof, the user is prompted to identify anatomical landmarks such as a pedicle or pedicle center, spinous process edge, midline axis, or intervertebral disc, as illustrated in FIG. 3. The user can identify the requested anatomical landmarks on the displayed medical image using any of a variety of computing input devices known in the art such as a mouse, keyboard, microphone, touchpad, touchscreen and the like, and a variety of input techniques known in the art such as a click, tap, selection, voice recognition and the like.

Once the user has identified one or all of the requested anatomical landmarks on the medical image, the user is similarly prompted to identify the matching anatomical landmark or landmarks on the displayed 3D representation of the patient's calibrated anatomy. The system 101 can thus determine whether the 3D representation is deficient based on information obtained from the identifying and matching processes. For instance, if requested anatomical landmarks are identified on the medical image but are not identifiable on the 3D representation, or anatomical landmarks identified on the medical image appear to have an unexpected size or positioning on the 3D representation, the system 101 can fix or generate a more accurate 3D representation, or recalibrate the size of the anatomy. The generation of the 3D representation of step 256, including the identifying and matching of anatomical landmarks, can be repeated until a 3D representation of adequate accuracy is generated. An adequately accurate 3D representation can be determined in real time by a user viewing the 3D representation, or using thresholds and/or rules that dictate the amount of deviation permitted between the 3D representation and the medical image. The final, resulting 3D representation can also be referred to as a "first image" or a "pre-operative image."

At step 258, the IMU-based assistance system 101 calculates operative parameters using the anatomical data from the pre-operative 3D representation generated at step 256. In some embodiments, the IMU-based assistance system calculates operative parameters using a statistical shape model of the anatomy and planned trajectory, and, in turn, morphs this model to fit the anatomy of the subject patient that is derived from the X-rays. Non-limiting examples of operative parameters include (1) an identification of the one or more bones or bone segments in which bone anchors are to be fixed, (2) bone anchor entry points, (3) target coordinates of the trajectories through which the bone anchors are to be driven, (4) and a depth to which the bone anchors are to be driven.

In turn, at step 258, IMU data is obtained by the IMU-based assistance system 101 from each of the IMUs 203 that are wirelessly coupled with the system 101. IMU data can include, for example, rotation matrices and translation vectors that describe detected data such as orientation and location. In the present exemplary embodiment, the IMUs 203 are a plurality of stand-alone IMUs including IMUs 103-2 and 103-n. Prior to obtaining the IMU data, in an intra-operative environment, the IMUs 203 are placed either on a surgical table or the patient, aligned in a particular orientation. That is, for example, the IMUs may be oriented in a way that they are aligned with the sagittal plane of the patient's anatomy, and perpendicular to gravity. The IMUs 203 can be positioned and/or aligned by a medical professional or the like that has access to the patient in the intra-operative environment. The IMUs 203 are then turned on and, in turn, the IMU data is transmitted to the system 101 by the IMUs' wireless communication means (e.g., Bluetooth). The IMU data can be reported unprompted by each of the IMUs 203 to the system 101, or can be requested by and transmitted to the system 101. The IMU data reported by the IMUs 203 includes information generated and collected by the sensors of each of the IMUs, such as the absolute location of each of the IMUs 203 and/or their relative locations.

At step 262, the IMU-based assistance system 101 prompts for an IMU-enabled surgical tool to be used to contact certain points on the patient's real-world anatomy. In some embodiments, the points that are to be contacted correspond to the anatomical landmarks described above in connection with step 256. By contacting these points, it is possible to match points in a real world space to the 3D model that has been generated and stored by the system 101. The prompting by the system 101 can be made via a display device of the system 101. For example, the IMU-based assistance system 101 can display a list of areas to be contacted using the IMU-based surgical tool, or can display those desired contact points on a visual representation of the patient's anatomy. It should be understood that the prompts can be performed one point at a time, such that each subsequent prompt is presented only after the point prompted for in the preceding prompt has been contacted. Or, all points can be prompted for using a single prompt.

At step 264, the IMU-enabled tool 103-1 that is used to contact the points prompted for at step 262 transmits contact information to the IMU-based assistance system 101. As discussed above, because the points to be contacted can be prompted for individually or as a group, the manner in which the contact information is transmitted can vary accordingly. Here, at step 264, the IMU-enabled tool 103-1 transmits information indicating that it has contacted a prompted-for point each time that the IMU-enabled tool 103-1 contacts such a point. The contact information transmitted by the IMU-enabled tool 103-1 for each contact point can include an indication that a point has been contacted and/or the coordinates of each specific point contacted on the patient's anatomy.

The coordinates of each contacted point are obtained from the sensors in the IMU of the IMU-enabled tool 103-1. These coordinates can indicate the location of each specific point of the patient's anatomy that is touched with the IMU-enabled surgical tools in space—e.g., relative to the IMUs positioned on the table or the patient. In turn, at step 266, the IMU-based assistance system 101 uses the information received at step 264 indicating coordinates of certain points on the patient's anatomy to determine and match the patient's real-world anatomy to the anatomy represented in the pre-operative image generated at step 256. This can be accomplished by correlating corresponding anatomical points or landmarks between the patient's real-world anatomy and the anatomy of the pre-operative 3D representation. Once the real-world anatomy has been matched to the pre-operative 3D representation, the system 101 is aware of or can determine the location of the patient's real-world anatomy and the IMU-enabled surgical tools, relative to one another and to the anatomy represented in the pre-operative 3D representation. Using this information, in an intra-operative environment, the IMU-based assistance system 101 can provide, apply or verify the application of the operative parameters calculated at step 258.

Once the patient's real-world anatomy has been matched to the patient's pre-operative 3D representation, the system 101 can provide an indication that the IMU-based assistance system 101 is ready to be used in conjunction with other tools. For instance, as shown in FIG. 2, a tool 204, such as a pedicle preparation tool, is to be used in an operative environment. The system 101 therefore can indicate that a tool 204 that is IMU-enabled is ready to be used.

Thus, at step 268, as the tool 204 is used in surgery, the IMU-based assistance system can provide a variety of intra-operative feedback. The intra-operative feedback can be determined based in part on the acquired or calculated operative parameters, the pre-operative 3D representative image, the patient anatomy matched to the 3D representation, and/or the IMU data. The feedback can be provided in real-time or substantially in real time with the use of the tool 204. It should be understood that the intra-operative feedback, and the information used to generate it such as the measured placement and operation of the tool (e.g., relative to the operative parameters), can be recorded in the memory of the system 101.

In some embodiments, the system 101, at step 268, displays a visual representation of the tool 204 and its location relative to the patient's anatomy or to the pre-operative 3D representative image. The location of the tool 204 can be obtained from location data generated by the sensors of the IMU of the tool 204, the patient's anatomy and/or the pre-operative 3D image (which, as described in connection with step 266, can match each other).

In some embodiments, the visual representation of the tool 204 can be shown, in real time or substantially in real time, superimposed over the pre-operative 3D image of the patient's anatomy. The calculated operative parameters can also be displayed in conjunction with the visual-representation of the tool 204. The system 101 can thus provide real-time feedback of the tool's location compared to the operative parameters. For instance, as the tool is operated, the display renders the trajectory of the visually represented tool as well as the target trajectory of the pre-operative image. Similarly, the visually represented tool can be shown along with the identified bone where bone anchors are to be fixed, bone anchor entry points, target depth of bone anchor, and the like. Displaying a visual representation of the tool in this manner allows for real-time feedback and correction of the operation of the tool to match the operative parameters. In some example embodiments, the system 101 can display other measurements of the IMU-enabled tool 204, such as angular measurements.

In some embodiments, the intra-operative feedback provided at step 268 includes notifications, warnings, or the like, indicating a certain amount of deviation of the IMU-enabled surgical tool operation from the calculated operative parameters.

Second Embodiment

Figure 4:
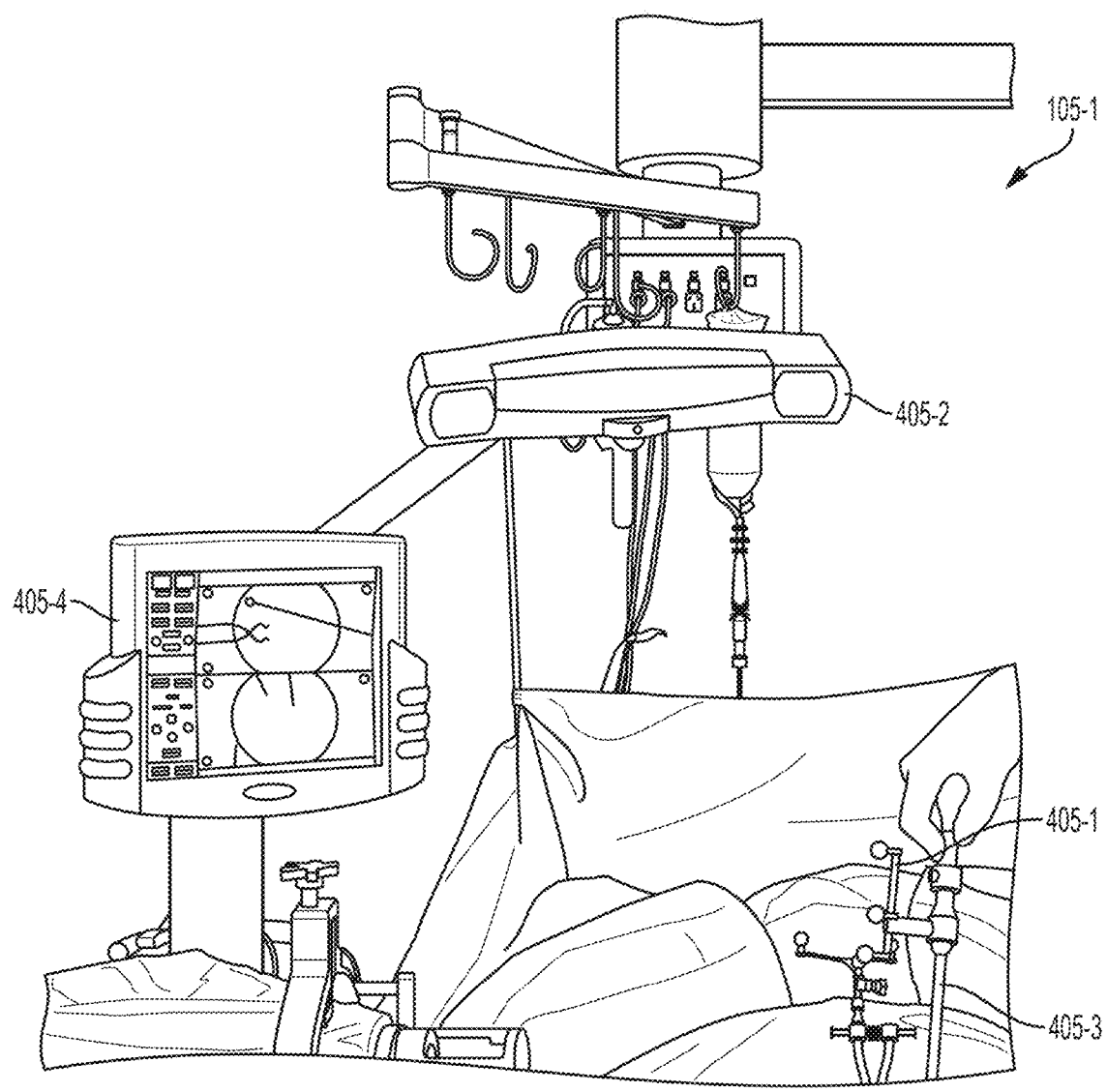
FIG. 4 illustrates an exemplary embodiment of another configuration of the IMU-based assistance system embedded in a surgical navigation system.

FIG. 4 illustrates another exemplary embodiment of a configuration of the IMU-based assistance system 101. In FIG. 4, the IMU-based assistance system 101 provides enhanced accuracy, such as error correction, to navigated surgery performed using the surgical navigation system 105-$n$. The IMU-based assistance system 101 in FIG. 4 is incorporated in the surgical navigation system 105-$n$, such that the system 101 shares hardware (e.g., processor and memory) and/or software resources of the navigation system 105-$n$. However, it should be understood that in some embodiments, the functionality of the systems 101 and 105-$n$ described in connection with FIG. 4 can be provided using a stand-alone IMU-based assistance system 101 and a stand-alone surgical navigation system 105-$n$ that are in communication with one another.

As described above in connection with FIG. 1, the surgical navigation system 105-$n$ is a system that includes a set of instruments (or tools) and devices that can be intra-operatively tracked with relation to the patient's anatomy. As shown in FIG. 4, the surgical navigation system 105-$n$ includes an instrument array 405-1, a camera 405-2, an instrument shaft 405-3, and a display device 405-4. It should be understood that, although not displayed in FIG. 4, the surgical navigation system 105-$n$ can include other types and numbers of instruments and devices.

Traditional surgical navigation systems track the location and positioning of its instruments using a camera to identify movement of the array relative to the camera. However, the accuracy of traditional navigation systems is decreased when instruments are rotated out of the cameras view, for instance, when an instrument array is flipped 180 degrees out of the line of sight of the camera. In this regard, to address drawbacks from traditional navigation systems, the surgical navigation system 105-$n$ additionally or alternatively includes IMUs equipped on the instrument array 405-1 and/or the instrument shaft 405-3.

While in some embodiments the IMUs can be added to instruments during manufacturing of the navigation system, in FIG. 4, IMUs are removably attached post-manufacture to the instrument array 405-1 and instrument shaft 405-3. As described above in further detail in connection with FIG. 2, IMUs include sensors that can measure and report attributes of the object to which they are attached. The IMU-enabled instrument array 405-1 and shaft 405-3 therefore include sensors within their respective IMUs that can collect information about their absolute location, rotation, angles, and the like, as well as these and other attributes of the instrument array 405-1 and shaft 405-3 relative to each other and to other instruments and devices of the navigation system 105-$n$ or relative to the patient.

In some embodiments, the IMU-enabled instruments 405-1 and 405-3 can report their measured data to the IMU-based assistance system 101. The measured data can be used to provide intra-operative feedback, such as error correction, in connection with the operation of the instruments, the patient's anatomy, imaging of the patient's anatomy, and calculating operative parameters. On the other hand, in some embodiments in which the IMU-enabled instrument array 405-1 and instrument shaft 405-3 are configured to operate in conjunction with camera 405-2, the IMU-enabled instruments can provide further accuracy and/or error correction as compared to use of the camera alone.

One non-limiting example of error correction includes applying correction factors when the IMU-based assistance system 101 and surgical navigation system 105-$n$ identify a potential for tracking errors, such as those resulting from line of sight challenges with visual navigation systems where the camera may lose site of the respective tracking array. The IMUs are able to detect relative angle change, and can report this change to the surgical navigation system 105-$n$. If the angle change is different than what the camera 405-2 measures, or if the camera can no longer see the instrument array, the 3-dimensional angle change measured by the IMUs is added to the last known position of the instrument before it left the field of view of the camera 405-2. The navigation system, in turn, displays an updated location and trajectory of the instrument until the instrument comes back into an accurate field of view for the camera 405-2. For instance, the surgical navigation system 105-*n* can detect that the instrument array 405-1 (or another instrument) has been rotated or angled away from the camera 405-2, or otherwise obscured, a large enough amount to likely induce error, as determined based on thresholds pre-identified or calculated in real-time. In such cases, the camera 405-2 is deemed to no longer be able to accurately measure the location and/or other attributes of the instrument array 405-1 with sufficient precision. The IMU-based assistance system 101 thus retrieves data from the IMUs of the IMU-enabled instruments in order to supplement the measurements of the tools obtained from the camera 405-2. In other words, once the instrument array 405-1 can no longer be reliably tracked by the camera 405-2, the sensors of the IMU-enabled instrument array 405-1 retrieve and transmit data to the system 101. The IMU-based assistance system 101 and the navigation system 105-*n* share their IMU data and camera positioning information to generate error-corrected information about the instruments 405-1 and 405-3, such as their positions. The error-corrected information about the instruments 405-1 and 405-3 allows the display 405-4 to continue to seamlessly display visual representations of one or more of the instruments, patient's anatomy, imaging of the patient's anatomy, or operative parameters.

By supplementing the instruments 405-1 and 405-3 with IMUs, the range of the navigation system 105-*n* can be extended by effectively increasing the field of view of the camera 405-2 and reducing or eliminating its blind spots.

Third Embodiment

Another exemplary embodiment of a configuration of the IMU-based assistance system 101 is used to provide visual tracking of surgical tools. In the present embodiment, the IMU based assistance system 101 provides navigation similar to that of the surgical navigation system 105-*n* described above in connection with FIG. 4, without requiring such a surgical navigation system and the high costs associated therewith.

Figure 5:
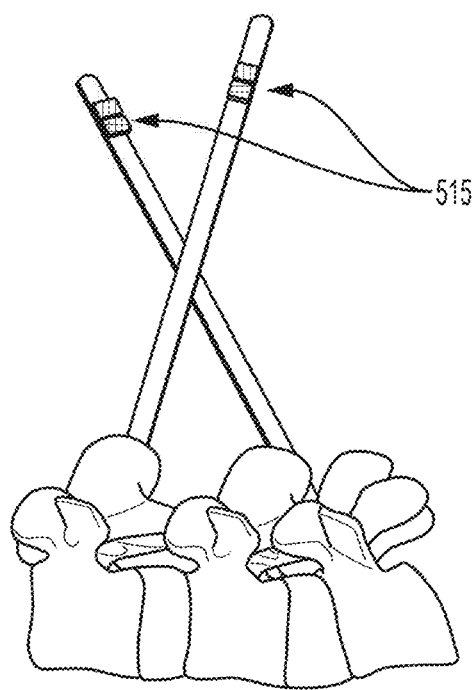
FIG. 5 is a side view of surgical instruments used with the IMU-based assistance system.

Instead, in the present exemplary embodiment, the IMU-based assistance system 101 includes a processor, memory, a display device, and a camera. The camera of the IMU-based assistance system can be housed together with the other components of the IMU-based assistance system 101, or can be provided as a separate device that is communicatively coupled (e.g., using Bluetooth) to the rest of the system 101. In some embodiments, the camera is statically positioned, such as a table-mounted camera. The IMU-based assistance system is in wireless communication with IMUs coupled to surgical instruments and/or implants. As shown in FIG. 5, the surgical instruments also have attached to them markers 515 such as spheres or flags having a color, pattern, combination, etc. that uniquely identifies the instrument, which as described below can be used to track the surgical instruments using a camera.

In an intra-operative environment, the camera of the IMU-based assistance system 101 can measure the position, angles, orientation, and other attributes of the instruments by identifying and tracking the markers attached or equipped on each instrument in images captured by the camera. Moreover, each of the IMUs of the IMU-enabled instruments can collect measurement data from its sensors and transmit it to the IMU-based assistance system 101. The IMU measurement data includes various measurements described above in connection with FIG. 2 of each of the IMU-enabled instruments relative to one another or to other IMUs.

As described above in connection with FIG. 4, the IMU-based assistance system 101 can supplement measurements obtained from the camera of the IMU-based assistance system 101 in the present embodiment with the IMU measurement data collected and reported by the IMUs of the IMU-enabled instruments. This way, blind spots and other line-of-sight issues resulting from a statically positioned camera of the system 101 can be reduced or eliminated by correcting inaccurate or error-prone camera measurement data with the IMU measurement data.

The display of the IMU-based assistance system 101, by supplementing the camera measurement data with the IMU measurement data can provide continuous intra-operative feedback even when the camera cannot accurately measure the position, angles, orientation and other attributes of the instruments.

In some embodiments, IMU measurement data can be used as primary navigation information and measurements obtained from the camera can be used to correct the IMU data as needed. For example, absolute position and/or orientation information obtained from the camera can be used periodically to correct drift error that may occur in relative position and/or orientation measurements obtained from the IMUs. In some embodiments, the IMUs can be omitted and the instruments can be tracked using only the markers and the camera.

Fourth Embodiment

Figure 6:
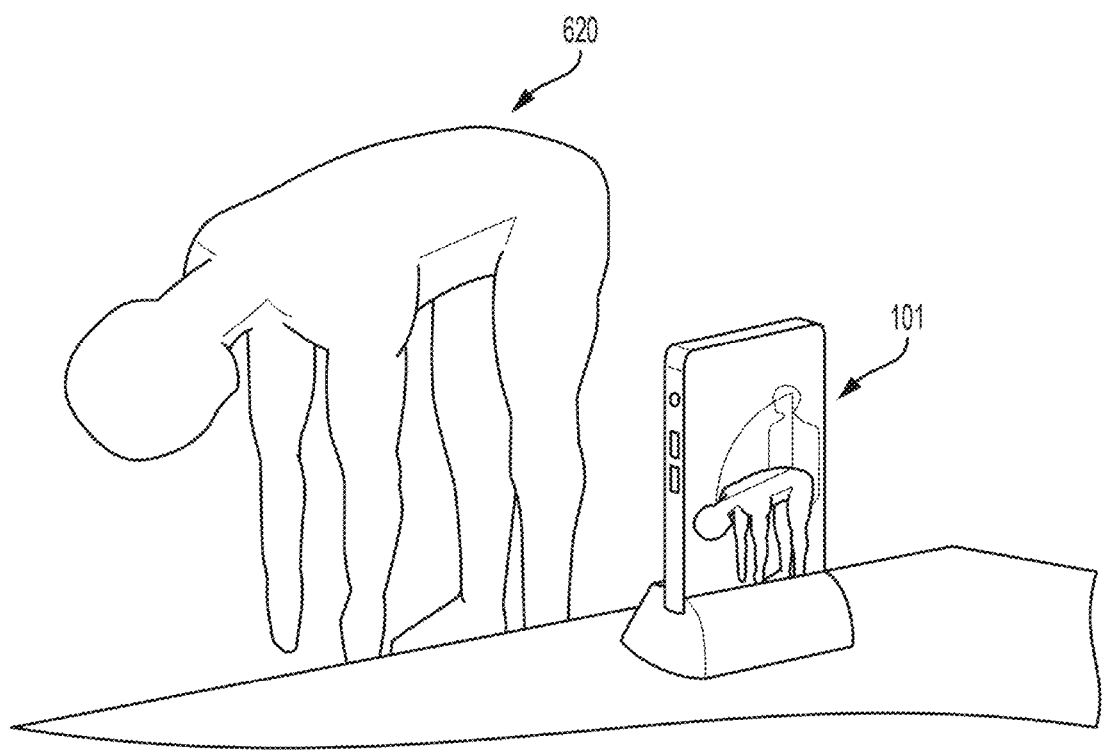
FIG. 6 illustrates an exemplary embodiment of another configuration of the IMU-based assistance system embedded in a personal computing device.

FIG. 6 illustrates another exemplary embodiment of a configuration of the IMU-based assistance system 101. In FIG. 6, the IMU-based assistance system 101 provides pre-operative planning, and intra- and post-operative assessment capabilities. As shown, the IMU-based assistance system 101 illustrated in FIG. 6 is provided in, or used in connection with, a smartphone, tablet or similar computing device.

In a pre-operative environment, one or more IMUs can be attached to the patient 620 to measure desired attributes about the patient 620. For instance, in a pre-operative environment for spinal surgery, IMUs can be attached, at the skin level, to the spine, pelvis, hips, head and/or thighs of the patient 620. Skin level refers to an area above or substantially adjacent to the patient's skin. Non-limiting examples of how IMUs are attached to the patient 620 include using straps, adhesive, or clothing apparel (e.g., shirt, vest) equipped with IMUs.

In turn, the patient's flexibility, range of motion, gait, or other parameters are measured by prompting the patient 620 to assume various physical positions, such as the bent-over position illustrated in FIG. 6. Prompting the patient 620 can be performed by displaying, via the display device of the IMU-based assistance system 101, the position to be assumed by the patient 620. In some embodiments, a camera of the system 101 can photograph or record the patient as he or she assumes a position to ensure that it matches the prompted-for position. In some embodiments, photographs or video recordings can be captured using a separate device and transmitted to the system 101 for processing. Once the patient 620 has assumed a position prompted for by the system 101, the IMU-based assistance system 101 retrieves and/or requests sensor data from the IMUs attached to the patient 620. The sensor data includes, among other things, the relative position of each of the IMUs attached to the patient 620. For example, using the retrieved and/or requested sensor data from the IMUs, the system 101 can calculate the relative position and/or angle of the patient's head and cervical spine relative to the patient's pelvis.

The patient's flexibility, range of motion, etc., as determined by the system 101 using the sensor data, can be compared against objective standards, which can be retrieved from the memory of the system 101, to diagnose the patient's condition and/or identify the patient's target or desired flexibility. A pre-operative plan, including for example a desired or target flexibility, can be determined, by a medical professional and/or a computing system (e.g., IMU-based assistance system 101) using objective standard measurements of flexibility.

Figure 7:
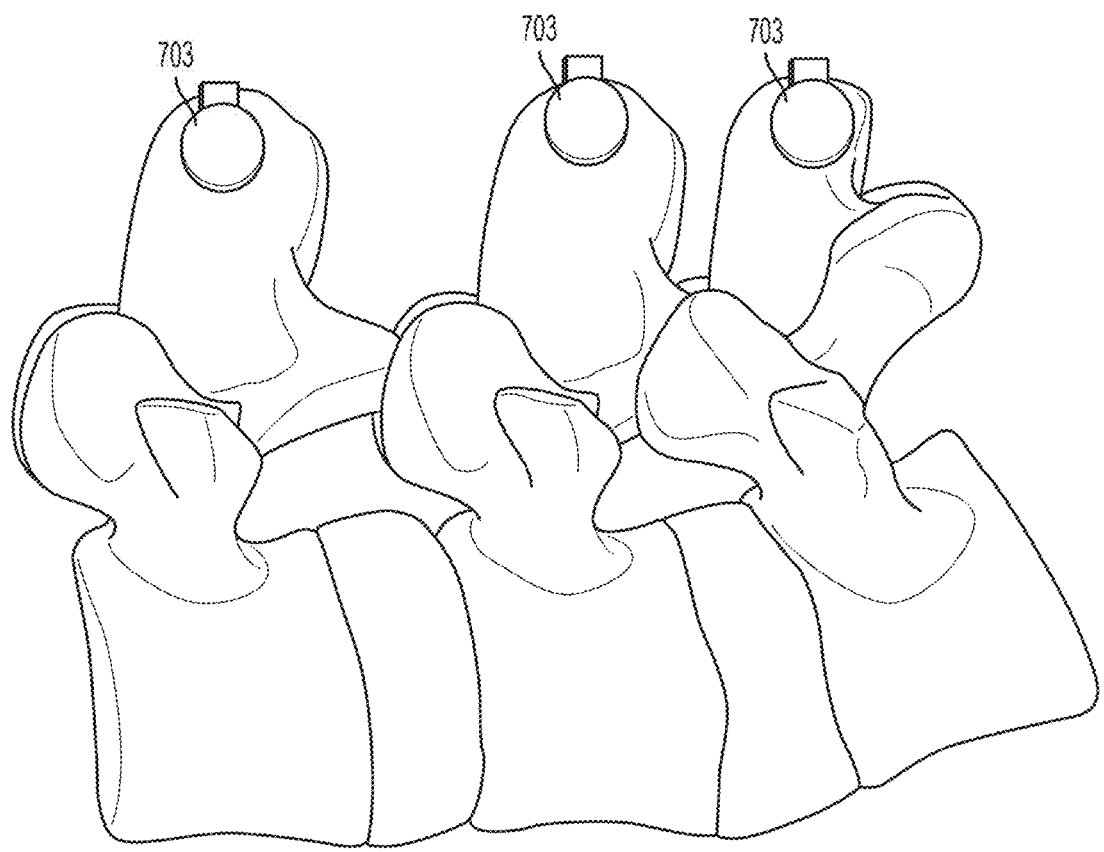
FIG. 7 is a side view of an exemplary embodiment of a section of a spine having attached IMUs.

In an intra-operative environment, the measurements of the patient 620 obtained pre-operatively can be used to assess the patient and, if needed, to make corrections as needed. More specifically, one or more of the IMU's attached to the patient pre-operatively can be left on the patient while the patient undergoes surgery. In some embodiments, additional IMUs can be attached to the patient. For example, during spinal surgery, IMUs can be attached to the patient's spine, at various spinal levels as shown in FIG. 7. That is, FIG. 7 illustrates IMUs 703 clipped or attached to each spinous process of each of a plurality of vertebrae.

In turn, during surgery, the IMU-based assistance system 101 can retrieve and/or request sensor data from the IMUs attached to the patient 620. The sensor data can be continuously transmitted from the IMUs to the IMU-based assistance system 101 throughout the surgery, in real-time or substantially in real-time. Additionally or alternatively, the sensor data can be transmitted from the IMUs to the IMU-based assistance system 101 upon request, for instance, when certain surgical milestones are reached during the surgery of the patient 620.

With reference to above-referenced spinal surgery example, the data transmitted from the IMUs to the IMU-based assistance system 101 intra-operatively can be used to measure a patient's attributes, such as angles of derotation, kyphosis/lordosis correction, distraction/compression, fracture reduction, etc. The intra-operatively measured attributes are compared to IMU data received pre-operatively and/or to a calculated pre-operative plan that includes target measurements and/or attributes of the patient. For instance, for artificial disc surgery, IMUs can be placed at different levels of the spine to obtain measurements to: set the spine in a proper position and ensure that endplates are properly selected to keep the patient's core neutral. For posterior cervical surgery, IMUs can be placed on the spine and the head of the patient to measure and calculate whether the patient's head is positioned properly and the patient's gaze angle is optimal. For surgery to correct spinal distraction, IMUs are placed on different levels above and below a pertinent disc space to measure, for example, disc space angle, and to determine the optimal cage size and angle.

In some embodiments, IMUs attached to multiple spinal levels are used to build a statistical shape model of the patient's spine in 3D. That is, the data generated by the IMUs 703 generate information about geometrical properties of the patient's spine. The IMU-based assistance system 101 generates the shape model and can track the correction of the spine in 3D without the need to obtain medical imaging. In another embodiment, IMUs attached to the patient's pelvis, spine, and/or femurs, for example, can be used to measure a patient's pelvic tilt pre- and intra-operatively. By comparing the two, the system 101 can determine whether the pelvic tilt has been corrected or how it has been changed relative to the pre-operative measurement or plan.

Post-operatively, the IMU-based assistance system 101 retrieves and/or requests sensor data from IMUs attached to the patient 620 at all or some of the parts of the patient where pre- or intra-operative IMUs were attached. The system 101 can calculate changes to the patient's attributes, such as flexibility and head positioning, by comparing the pre- and/or intra-operative measurements obtained by the system 101 via the IMUs attached to the patient 620 to the post-operative sensor data. This comparison yields the patient's development and/or progress. The system 101 provides confirmation of whether or not the target corrections to the patient were achieved by the operation.

The IMU-based assistance system 101 provides feedback by displaying, via its display device, text and/or graphics indicating one or more of the patient's pre-, intra- or post-operative measurements, and/or the patient's pre-operative plan. For example, the display device of the system 101 provides an illustration of the patient in a pre-operatively assumed position. The illustration of the patient 620 can include measurements obtained from the data produced by the IMUs attached to the patient, including positions, angles, and/or curves of or between certain regions of the patient's body to which the IMUs were attached. The system 101 can also illustrate the patient in the same position assumed intra- or post-operatively, together with the same measurements of the patient 620 displayed with the pre-operative image. Moreover, the system 101 can display measurements and/or illustrations of the patient in accordance with the pre-operative plan. Such a display allows a medical professional or other operator of the system 101 to visualize the progress achieved by the operation.

Fifth Embodiment

Figure 8:
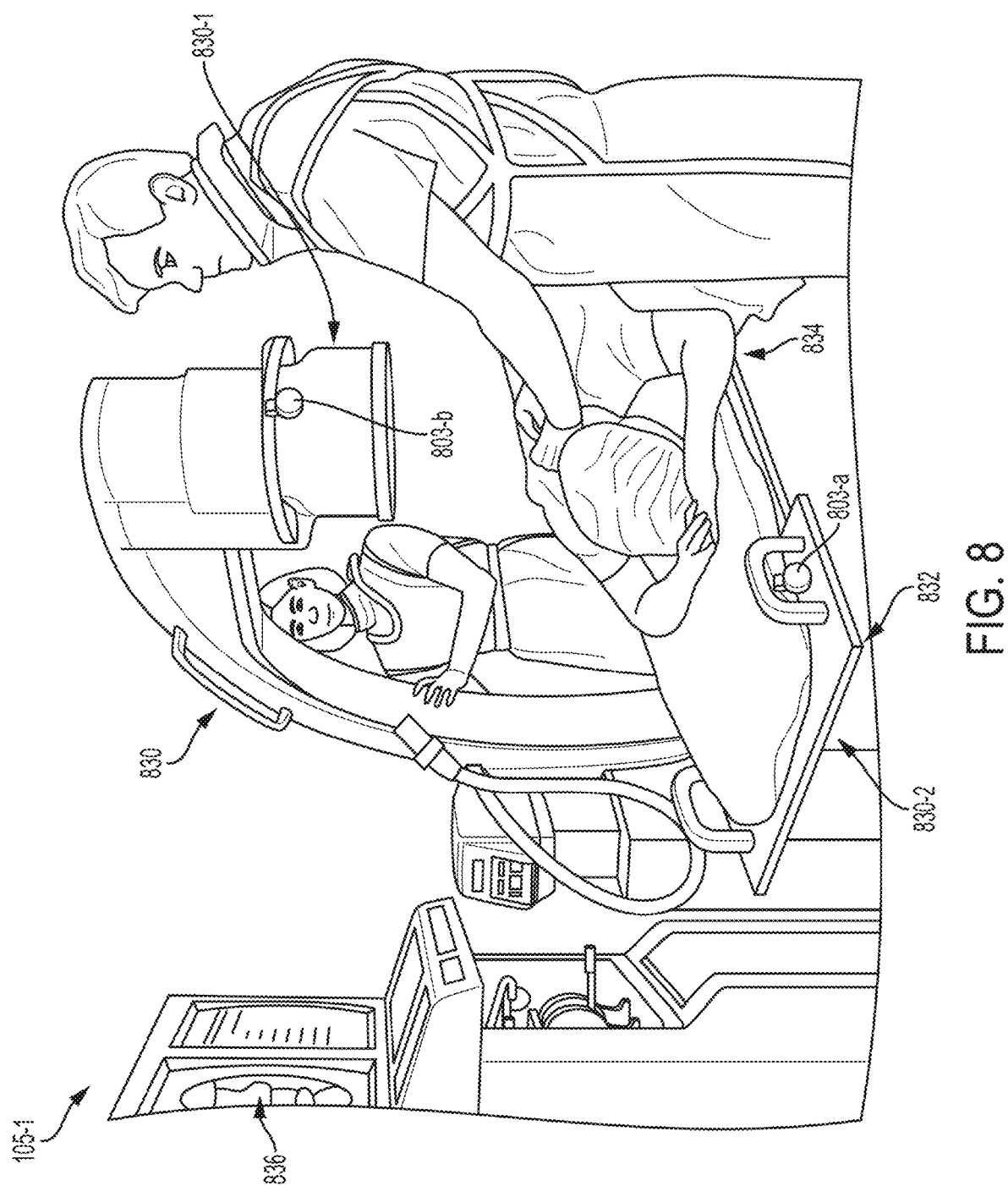
FIG. 8 illustrates an exemplary embodiment of another configuration of the IMU-based assistance system embedded in a C-arm imaging system.

FIG. 8 illustrates another exemplary embodiment of a configuration of the IMU-based assistance system 101. In FIG. 8, the IMU-based assistance system 101 provides accurate alignment of surgical systems such as the C-arm system 105-1. The IMU-based assistance system 101 in FIG. 8 is incorporated in the C-arm system 105-1, such that the system 101 shares hardware and/or software resources of the C-arm system 105-1. However, it should be understood that in some embodiments, the functionality of the systems 101 and 105-1 described in connection with FIG. 8 can be provided using a stand-alone IMU-based assistance system 101 and a stand-alone C-arm system 105-1 that are in communication with one another.

The C-arm system 105-1 is a fluoroscopic X-ray system that is used to provide real-time medical images of a patient 834, for example, during an operation on the patient. The C-arm system 105-1 includes a C-shaped arm connecting an X-ray detector 830-1 to an X-ray source 830-2 (also referred to as an "X-ray emitter"), which is not visible in FIG. 8 but is positioned below the surgical table 832. It should be understood that in some embodiments, the location of the X-ray source 830-1 and X-ray detector 830-2 can be reversed so that each is on a different end of the C-shaped arm 830 than as displayed in FIG. 8. The C-arm system 105-1 also includes a display device that can be used to input and output information. For instance, the display device can output medical images of the patient 834, and receive inputs such as manipulations of the images of the patient. Although not illustrated in FIG. 8, the C-arm system 105-1 includes one or more processors and memory, and can include other types and numbers of devices.

The C-shaped arm 830 of the C-arm system 105-1 can be moved and rotated in a variety of ways known by those skilled in the art, in order to position the C-shaped arm 830 at a desired location. In some embodiments, the C-shaped arm can be moved horizontally, vertically and around a swivel axis, allowing images of the patient 834 to be obtained from practically any angle. While the C-shaped arm 830 can be positioned manually, in some embodiments, the C-shaped arm 830 can be automatically driven by the C-arm system 105-1 using a combination of motors, wheels and other motion mechanisms attached to the C-shaped arm 830. Nonetheless, traditionally, the desired location to which the C-shaped arm 830 is to be driven must be identified or determined each time that the C-shaped arm 830 is to be placed for imaging of the patient 834, and the C-shaped arm 830 must be manually moved or driven to that position. Positioning of the C-shaped arm has traditionally been a critical and time-consuming process, easily susceptible to human error.

In some embodiments, C-arm systems such as C-arm system 105-1 have a scanning capability that is integrated with a connected navigation system. Once the reference array is placed on the patient, a ring with fiducials that can be seen by the navigation camera is placed on the C-arm emitter. The C-arm is powered, and can perform a scan on the patient of over 180 degrees without being driven by an operator. During this 180 degree (or 180+ degree) scan, the C-arm takes multiple images, and feeds them into the navigation system to be reconstructed into a 3D model. The camera sees each position of the C-arm relative to the patient anatomy, and uses these to orient the navigated instruments to the reconstructed 3D anatomy in the virtual image.

Figure 9:
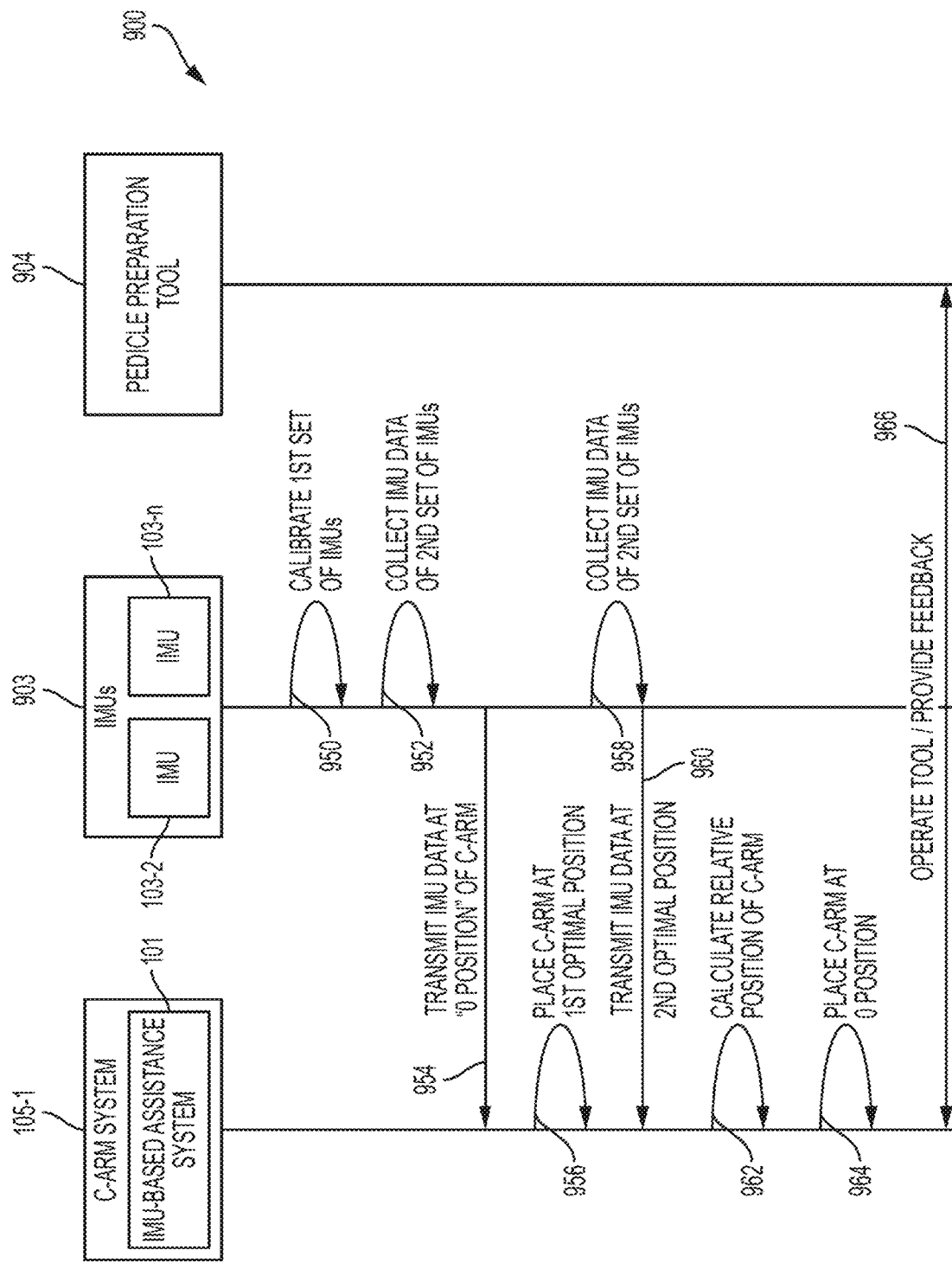
FIG. 9 is a sequence diagram of an exemplary embodiment of a process for using the configuration of the IMU-based assistance system embedded in the C-arm imaging system.

To obtain an optimal image of the relevant area of the anatomy of the patient 834, the C-shaped arm 830 must be positioned at a precise location and angle relative to the patient 834. In some embodiments, during spinal surgery, the optimal position of the C-shaped arm 830 is a position where the patient facing side of the X-ray detector 830-1 is parallel to the spine plane and/or the X-ray is emitted perpendicular to the spine plane of the patient 834. Because the spine plane is different between each vertebral level, the C-shaped arm 830 must be placed in a unique position for each vertebral level. As shown in FIG. 9, the IMU-based assistance system 101 incorporated in the C-arm system 105-1 enables automated alignment of the C-shaped arm 830 using IMUs.

FIG. 9 illustrates a sequence diagram for providing IMU-assisted alignment of the C-arm system 105-1. As shown in FIG. 9, the IMU-based assistance system 101 is incorporated in the C-arm system 105-1. The C-arm system 105-1 is in wireless communication with the IMUs 803. Among the IMUs 903 are IMUs 103-2 and 103-n illustrated in FIG. 1. As described in further detail below, the IMUs 903 include two sets of IMUs: one set positioned on or attached to the patient and/or operating table, and another set attached to portions of the C-arm system 105-1. The C-arm system 105-1 is also in wireless communication with the tool 904, such as a pedicle preparation tool. It should be understood that tools other than and/or in addition to the pedicle preparation tool 904 can be in communication with the C-arm system 105-1.

In the example embodiment described in connection with FIG. 9, the C-arm system 105-1 is used for an operation of the spine. FIG. 9 describes an exemplary process for optimally aligning and realigning the C-arm system 105-1 such that each pedicle of the patient is accurately targeted by the C-arm 105-1. That is, the exemplary process of FIG. 9 can measure the positioning of the C-arm system 105-1 and replicate that position.

At step 950, a first set of IMUs 903-a from among the IMUs 903 is turned on an calibrated. The first set of IMUs 903-a are IMUs that are placed or attached to the patient or the surgical table. As described above in connection with FIG. 2, the IMUs 903-a can be placed in particular orientations such as on or near anatomical landmarks of the patient. For example, the IMUs 903a can be positioned on the surgical table similar to IMU 803-a shown in FIG. 8.

Once the IMUs 903-a are placed and turned on, they can be calibrated by reporting to each other and/or to the IMU-based assistance system 101 respective IMU data. The IMU data reported by each of the IMUs 903-a includes each IMU's location information. The IMUs 903-a and/or the IMU-based assistance system 101 can calculate the location or position of each IMU relative to each other and/or relative to the ground. By calibrating the IMUs 903-a, it is possible to understand or determine their location in space, and thus the location of other IMUs relative to that space.

In turn, at step 952, IMU data is collected by each IMU of a second set of IMUs 903-b. The second set of IMUs 903-b is made up of IMUs from the IMUs 903. Moreover, the second set of IMUs 903-b is made up of IMUs that are placed or attached to portions of the C-arm system 105-1. For example, the second set of IMUs 903-b can be made up of IMUs positioned on the X-ray source and/or the X-ray detector, similar to IMU 803-b shown in FIG. 8. The IMU data collected at step 952 includes information measured by each sensor of the IMUs 903-b.

When the data is collected from the IMUs 903-b at step 952, the C-shaped arm of the C-arm system 105-1 is positioned such that the X-ray emitter and/or the X-ray detector are or substantially parallel to the ground. In other words, the X-ray emitter and/or X-ray detector being parallel to the ground means that their respective patient-side faces are substantially parallel to the ground. This position of the C-arm system 105-1 is also referred to as a "'0'position." At step 954, the IMU data collected by the IMUs 903-b at step 952 while the C-arm system 105-1 is in the 0 position is transmitted to the IMU-based assistance system 101, which stores the received 0 position IMU data.

In turn, at step 956, the C-shaped arm of the C-arm system 105-1 is moved to a first optimal position. The first optimal position is a position in which the C-arm system 105-1 is best aligned to view and/or image a selected pedicle in the patient's spine or other anatomy of interest, as known by those skilled in the art. Once the C-arm system 105-1 has been placed in the first optimal position, the second set of IMUs 903-b attached to the C-arm system 105-1 collect IMU data from their sensors at step 958. In some embodiments, collection of the IMU data is triggered by the C-arm system 105-1 indicating to the IMUs 903-b that the C-shaped arm is in the first optimal position.

The data collected by the IMUs 903-b at step 958 includes information indicating the position of the C-shaped arm of the C-arm system 105-1. The data collected at step 958 is in turn transmitted to the IMU-based assistance system 101 at step 960. In turn, at step 962, the system 101 calculates the relative position of the C-shaped arm in the first optimal position relative to the 0 position and/or to the position of the IMUs 903-a. Calculating the relative position of the C-shaped arm in the first optimal position is based on the IMU data received at step 960 and the 0 position data received at step 954.

In the intra-operative environment, the C-shaped arm of the C-arm system 105-1 is removed from the first optimal position and returned to the 0 position at step 964, such that the patient can be operated on without obstruction. When desired, the C-arm system 105-1 can be automatically returned to the alignment indicated by the recorded first optimal position. Because the first optimal position is a position of the C-shaped arm relative to the patient and/or the surgical table, the C-arm system 105-1 can always be accurately returned to the first optimal position, thereby reducing or eliminating the potential for error and wasted time.

With the C-arm system 105-1 removed, the IMU-enabled surgical instruments, such as the pedicle preparation tool 904, can be used to prepare, size and implant the bone anchor into the pedicle. The location of the pedicle preparation tool 904 is identifiable from the data produced by its sensors. Moreover, the location of the pedicle preparation tool 904 relative to the patient and/or the surgical table can be calculated from the data of the IMUs of the preparation tool 904 and the data of the first set of IMUs 903-*a*.

At step 966, the display device of the C-arm system 105-1, similar to the display device 836 illustrated in FIG. 8, is used to provide intra-operative feedback as the pedicle preparation tool 904 is operated. The intra-operative feedback can be continuously provided by the display device or can be provided when requested.

The display device of the C-arm system can render visual and numeric cues to guide the IMU-enabled pedicle preparation tool 904 to the desired portion of the patient's pedicle. The IMU-based assistance system 101 can determine the location of the pedicle preparation tool 904 relative to the patient's pedicle, an image of the patient, and/or the actual patient based on one or more of (1) the data produced by the IMUs of the tool 904, (2) the data produced by the first set of IMUs 903-*a* which define the absolute and relative location of the patient and/or surgical table, and (3) the data produced by the IMUs 903-*b* which defines the absolute and relative location of a pedicle of the patient.

In some embodiments, it is desirable to position the pedicle preparation tool 904 down the center of the pedicle in a direction perpendicular to the face of the X-ray source or X-ray detector of the C-arm system 105-1. In such cases, the display device provides feedback, to position the pedicle preparation tool 904 at the desired area of the pedicle, based on the IMU data received at step 960 in connection with the first optimal position of the C-arm system 105-1. Other examples of providing intra-operative feedback are described above in connection with FIG. 2.

Steps 956 to 966 of FIG. 9 can be repeated for each additional pedicle of the patient's spine. That is, at step 956, the C-shaped arm of the C-arm system 105-1 is instead moved to a second optimal position in which the C-shaped arm is aligned to best view and/or image the patient's next pedicle.

Although not illustrated in FIG. 9, the relative position of the C-arm system 105-1 in each optimal position can be recorded in connection with each corresponding pedicle of the patient. The recorded information can be added to a database of common pedicle angles that can later be used to calculate or predict likely positions of the C-arm system 105-1 for specific pedicles.

The example embodiments described above, including the systems and procedures depicted in or discussed in connection with FIGS. 1-9, or any part or function thereof, may be implemented by using hardware, software or a combination of the two. The implementation may be in one or more computers or other processing systems. While manipulations performed by these example embodiments may have been referred to in terms commonly associated with mental operations performed by a human operator, no human operator is needed to perform any of the operations described herein. In other words, the operations may be completely implemented with machine operations. Useful machines for performing the operation of the example embodiments presented herein include general purpose digital computers or similar devices.

Portions of the example embodiments described herein may be conveniently implemented by using a conventional general purpose computer, a specialized digital computer and/or a microprocessor programmed according to the teachings of the present disclosure, as is apparent to those skilled in the computer art. Appropriate software coding may readily be prepared by skilled programmers based on the teachings of the present disclosure.

Some embodiments may also be implemented by the preparation of application-specific integrated circuits, field programmable gate arrays, or by interconnecting an appropriate network of conventional component circuits.

Some embodiments include a computer program product. The computer program product may be a non-transitory storage medium or media having instructions stored thereon or therein which can be used to control, or cause, a computer to perform any of the procedures of the example embodiments described herein. The storage medium may include without limitation a floppy disk, a mini disk, an optical disc, a Blu-ray Disc, a DVD, a CD or CD-ROM, a micro drive, a magneto-optical disk, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the non-transitory computer readable medium or media, some implementations include software for controlling both the hardware of the general and/or special computer or microprocessor, and for enabling the computer or microprocessor to interact with a human user or other mechanism utilizing the results of the example embodiments described herein. Such software may include without limitation device drivers, operating systems, and user applications. Ultimately, such computer readable media further includes software for performing example aspects of the systems and methods described above.

Included in the programming and/or software of the general and/or special purpose computer or microprocessor are software modules for implementing the procedures described above.

While various example embodiments have been described above, it should be understood that they have been presented by way of example, and not limitation. It is apparent to persons skilled in the relevant art(s) that various changes in form and detail can be made therein. Thus, the disclosure should not be limited by any of the above described example embodiments.

In addition, it should be understood that the figures are presented for example purposes only. The architecture of the example embodiments presented herein is sufficiently flexible and configurable, such that it may be utilized and navigated in ways other than that shown in the accompanying figures.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

One skilled in the art will appreciate further features and advantages of the disclosure based on the above-described embodiments. Accordingly, the disclosure is not to be limited by what has been particularly shown and described. All publications and references cited herein are expressly incorporated herein by reference in their entirety.

What is claimed is:

1. A system for providing operative feedback, comprising:
a processor operable to:
receive, from an imaging device, one or more medical images, the one or more medical images representing (1) one or more views of a patient anatomy, and (2) one or more markers of a known size;
calibrate the size of the patient anatomy represented in the one or more medical images based on the known size of each of the one or more markers;
generate a three-dimensional (3D) representation of the patient anatomy based on:
(1) one or more anatomical images that match the patient anatomy represented in the one or more medical images, and
(2) one or more anatomical landmarks identified on both of the one or more medical images and the 3D representation;
calculate operative parameters based on the 3D representation of the patient anatomy;
receive first inertial measurement unit (IMU) data from a first set of IMUs positioned in an intra-operative environment, the first IMU data defining a location of each of the first set of IMUs in the intra-operative environment;
receive second IMU data from a second set of IMUs corresponding to one or more IMU-enabled tools, the second IMU data including a location of each of the one or more IMU-enabled tools relative to the locations of the first set of IMUs;
match the patient anatomy to the 3D representation based on second IMU data that is obtained when at least one of the one or more IMU-enabled tools contacts points of the patient anatomy; and
output operational feedback based on the operative parameters, the patient anatomy matched to the 3D representation, and the second IMU data, the operational feedback including an indication of an updated location of at least one of the one or more IMU-enabled tools with respect to at least one of (1) the operative parameters, (2) the patient anatomy, or (3) the 3D representation.

2. The system of claim 1, wherein the processor is operable to identify the one or more anatomical images that match the patient anatomy from among a set of existing anatomical images stored in a communicatively coupled database or atlas.

3. The system of claim 2, wherein the processor is operable to generate the 3D representation by matching the one or more anatomical images to the patient anatomy using a best fit method.

4. The system of claim 2, further comprising at least one memory communicatively coupled to the processor, the at least one memory being operable to store the database or atlas.

5. The system of claim 1, wherein the operative parameters include one or more of (1) a bone anchor insertion location, (2) a bone anchor trajectory, and (3) a bone anchor depth.

6. The system of claim 1, wherein the first set of IMUs are configured to be positioned on the patient and/or a surgical table corresponding to the patient in a first orientation relative to the patient.

7. The system of claim 6, wherein the first IMU data includes the absolute location of each of the IMUs.

8. The system of claim 7, wherein the processor is further operable to calculate the relative location of each of the IMUs in the first set of IMUs based on the first IMU data.

9. The system of claim 7, wherein the first IMU data includes the relative location of each of the IMUs.

10. The system of claim 1, wherein matching the real-world anatomy of the patient to the 3D representation comprises:
providing prompts to contact points on patient anatomy using one of the one or more IMU-enabled tools, and
associating the contact points of the patient anatomy to corresponding points on the 3D representation.

11. The system of claim 1, wherein the output of the operational feedback causes the operational feedback to be rendered on a display device.

12. The system of claim 11, wherein the operational feedback comprises a visual representation of the one or more IMU-enabled tools superimposed over the 3D representation, at respective locations of the one or more IMU-enabled tools relative to the patient anatomy.

13. The system of claim 12, wherein the operational feedback further comprises visual representations of the operative parameters.

14. A method for providing operative feedback, comprising:
receiving, from an imaging device, one or more medical images, the one or more medical images representing (1) one or more views of a patient anatomy, and (2) one or more markers of a known size;
calibrating, via a processor, the size of the patient anatomy represented in the one or more medical images based on the known size of each of the one or more markers;
generating, via the processor, a three-dimensional (3D) representation of the patient anatomy based on:
(1) one or more anatomical images that match the patient anatomy represented in the one or more medical images, and
(2) one or more anatomical landmarks identified on the one or more medical images and the 3D representation;
calculating, via the processor, operative parameters based on the 3D representation of the patient anatomy;
receiving, via the processor, first inertial measurement unit (IMU) data from a first set of IMUs positioned in an intra-operative environment, the first IMU data defining a location of each of the first set of IMUs in the intra-operative environment;
receiving, via the processor, second IMU data from a second set of IMUs corresponding to one or more IMU-enabled tools, the second IMU data including a location of each of the one or more IMU-enabled tools relative to the locations of the first set of IMUs;

matching, via the processor, the patient anatomy to the 3D representation based on second IMU data that is obtained when at least one of the one or more IMU-enabled tools contacts points of the patient anatomy; and outputting operational feedback based on the operative parameters, the patient anatomy matched to the 3D representation, and the second IMU data, the operational feedback including an indication of an updated location of at least one of the one or more IMU-enabled tools with respect to at least one of (1) the operative parameters, (2) the patient anatomy, or (3) the 3D representation.

15. The method of claim 14, wherein the one or more anatomical images that match the patient anatomy are identified from among a set of existing anatomical images stored in a database or atlas communicatively coupled to the processor.

16. The method of claim 15, wherein generating the 3D representation includes matching the one or more anatomical images to the patient anatomy using a best fit method.

17. The method of claim 14, wherein the operative parameters include one or more of (1) a bone anchor insertion location, (2) a bone anchor trajectory, and (3) a bone anchor depth.

18. The method of claim 14, wherein the first set of IMUs are positioned on the patient and/or a surgical table corresponding to the patient in a first orientation relative to the patient.

19. The method of claim 18, wherein the first IMU data includes the absolute location of each of the IMUs.

20. The method of claim 19, wherein the processor is further operable to calculate the relative location of each of the IMUs in the first set of IMUs based on the first IMU data.

21. The method of claim 19, wherein the first IMU data includes the relative location of each of the IMUs.

22. The method of claim 14, wherein matching the patient anatomy to the 3D representation comprises:

providing prompts to contact points on the patient anatomy using one of the one or more IMU-enabled tools, and associating the contact points of the patient anatomy to corresponding points on the 3D representation.

23. The method of claim 14, wherein the output of the operational feedback causes the operational feedback to be rendered on a display device.

24. The method of claim 23, wherein the operational feedback comprises a visual representation of the one or more IMU-enabled tools superimposed over the 3D representation, at respective locations of the one or more IMU-enabled tools relative to the patient anatomy.

25. The method of claim 24, wherein the operational feedback further comprises visual representations of the pre-operative parameters.

* * * * *